(12) United States Patent
Fitzgerald et al.

(10) Patent No.: US 11,654,276 B2
(45) Date of Patent: *May 23, 2023

(54) CATHETER PUMP

(71) Applicant: TC1 LLC, St. Paul, MN (US)

(72) Inventors: Keif M. Fitzgerald, San Jose, CA (US); Richard L. Keenan, Livermore, CA (US); William J. Harrison, Signal Mountain, TN (US)

(73) Assignee: TC1 LLC, St. Paul, MN (US)

( * ) Notice: Subject to any disclaimer, the term of this patent is extended or adjusted under 35 U.S.C. 154(b) by 278 days.

This patent is subject to a terminal disclaimer.

(21) Appl. No.: 17/086,377

(22) Filed: Oct. 31, 2020

(65) Prior Publication Data
US 2021/0046229 A1    Feb. 18, 2021

Related U.S. Application Data

(60) Continuation of application No. 16/110,648, filed on Aug. 23, 2018, now Pat. No. 11,058,865, which is a
(Continued)

(51) Int. Cl.
*A61M 60/857* (2021.01)
*A61M 60/13* (2021.01)
(Continued)

(52) U.S. Cl.
CPC .......... *A61M 60/857* (2021.01); *A61M 60/13* (2021.01); *A61M 60/174* (2021.01);
(Continued)

(58) Field of Classification Search
None
See application file for complete search history.

(56) References Cited

U.S. PATENT DOCUMENTS

| 1,902,418 A | 3/1933 | Pilgrim |
| 2,356,659 A | 8/1944 | Paiva |
| (Continued) | | |

FOREIGN PATENT DOCUMENTS

| CA | 2701810 A1 | 4/2009 |
| EP | 0453234 A1 | 10/1991 |
| (Continued) | | |

OTHER PUBLICATIONS

International Search Report and Written Opinion received in International Patent Application No. PCT/US2015/026025, dated Oct. 22, 2015, in 12 pages.
(Continued)

*Primary Examiner* — Michael W Kahelin
*Assistant Examiner* — Elizabeth K So
(74) *Attorney, Agent, or Firm* — Armstrong Teasdale LLP

(57) ABSTRACT

A catheter pump is provided that includes a rotatable impeller and an elongate cannula. The elongate cannula has a mesh that has a plurality of circumferential members disposed about the impeller. The elongate cannula has a plurality of axial connector extending between a proximal side of a distal circumferential member and a distal side of a proximal circumferential member. The circumferential members are radially self-expandable. The cannula is configured to minimize fracture within at least in the distal zone of the mesh as the elongated cannula moves into a sheathing device.

20 Claims, 17 Drawing Sheets

Related U.S. Application Data division of application No. 15/172,664, filed on Jun. 3, 2016, now Pat. No. 10,086,121, which is a division of application No. 13/801,528, filed on Mar. 13, 2013, now Pat. No. 9,358,329.

(60) Provisional application No. 61/667,903, filed on Jul. 3, 2012.

(51) Int. Cl.
*A61M 60/174* (2021.01)
*A61M 60/216* (2021.01)
*A61M 60/81* (2021.01)
*A61M 60/148* (2021.01)
*A61M 60/414* (2021.01)
*A61M 60/825* (2021.01)
*A61M 60/508* (2021.01)
*A61M 60/411* (2021.01)

(52) U.S. Cl.
CPC ........ *A61M 60/216* (2021.01); *A61M 60/411* (2021.01); *A61M 60/508* (2021.01); *A61M 60/81* (2021.01); *A61M 60/825* (2021.01); *A61M 60/148* (2021.01); *A61M 60/414* (2021.01)

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Shearman |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon |
| D264,134 S | 4/1982 | Xanthopoulos |
| 4,382,199 A | 5/1983 | Isaacson |
| 4,392,836 A | 7/1983 | Sugawara |
| 4,458,366 A | 7/1984 | Macgregor et al. |
| 4,537,561 A | 8/1985 | Xanthopoulos |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,673,334 A | 6/1987 | Allington et al. |
| 4,686,982 A | 8/1987 | Nash |
| 4,696,667 A | 9/1987 | Masch |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffmann et al. |
| 5,021,048 A | 6/1991 | Buckholtz |
| 5,044,902 A | 9/1991 | Malbec |
| 5,045,072 A | 9/1991 | Castillo et al. |
| 5,049,134 A | 9/1991 | Golding et al. |
| 5,059,174 A | 10/1991 | Vaillancourt |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte, Jr. et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,197 A | 2/1995 | Lemon et al. |
| 5,393,207 A | 2/1995 | Maher et al. |
| 5,405,341 A | 4/1995 | Martin |
| 5,405,383 A | 4/1995 | Barr |
| 5,415,637 A | 5/1995 | Khosravi |
| 5,437,541 A | 8/1995 | Vainrub |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,554,114 A | 9/1996 | Wallace et al. |
| 5,586,868 A | 12/1996 | Lawless et al. |
| 5,588,812 A | 12/1996 | Taylor et al. |
| 5,609,574 A | 3/1997 | Kaplan et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson, Jr. et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |

(56) References Cited

U.S. PATENT DOCUMENTS

| | | |
|---|---|---|
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens et al. |
| 5,868,703 A | 2/1999 | Bertolero et al. |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,927,956 A | 7/1999 | Lim et al. |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 5,993,420 A | 11/1999 | Hyman et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III |
| 6,053,705 A | 4/2000 | Schoeb et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,109,895 A | 8/2000 | Ray et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,203,528 B1 | 3/2001 | Deckert et al. |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,494,694 B1 | 12/2002 | Lawless et al. |
| 6,503,224 B1 | 1/2003 | Forman et al. |
| 6,508,777 B1 | 1/2003 | Macoviak et al. |
| 6,508,787 B2 | 1/2003 | Reimund et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | Deblanc et al. |
| 6,565,598 B1 | 5/2003 | Lootz |
| 6,572,349 B2 | 6/2003 | Sorensen et al. |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Gruendeman et al. |
| 6,794,784 B2 | 9/2004 | Takahashi et al. |
| 6,794,789 B2 | 9/2004 | Siess et al. |
| 6,814,713 B2 | 11/2004 | Aboul Hosn et al. |
| 6,817,836 B2 | 11/2004 | Nose et al. |
| 6,818,001 B2 | 11/2004 | Wulfman et al. |
| 6,835,049 B2 | 12/2004 | Ray |
| 6,860,713 B2 | 3/2005 | Hoover |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,962,488 B2 | 11/2005 | Davis et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,018,182 B2 | 3/2006 | O'Mahony et al. |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,214,038 B2 | 5/2007 | Saxer et al. |
| 7,229,258 B2 | 6/2007 | Wood et al. |
| 7,238,010 B2 | 7/2007 | Hershberger et al. |
| 7,241,257 B1 | 7/2007 | Ainsworth et al. |

(56) References Cited

U.S. PATENT DOCUMENTS

| | | |
|---|---|---|
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,478,999 B2 | 1/2009 | Limoges |
| 7,491,163 B2 | 2/2009 | Viole et al. |
| 7,534,258 B2 | 5/2009 | Gomez et al. |
| 7,605,298 B2 | 10/2009 | Bechert et al. |
| 7,619,560 B2 | 11/2009 | Penna et al. |
| 7,633,193 B2 | 12/2009 | Masoudipour et al. |
| 7,645,225 B2 | 1/2010 | Medvedev et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,934,912 B2 | 5/2011 | Voltenburg, Jr. et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 3,012,079 A1 | 9/2011 | Delgado, III |
| 8,025,647 B2 | 9/2011 | Siess et al. |
| 8,052,399 B2 | 11/2011 | Stemple et al. |
| 8,062,008 B2 | 11/2011 | Voltenburg, Jr. et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,142,400 B2 | 3/2012 | Rotem et al. |
| 8,177,703 B2 | 5/2012 | Smith et al. |
| 8,206,350 B2 | 6/2012 | Mann et al. |
| 8,216,122 B2 | 7/2012 | Kung et al. |
| 8,236,040 B2 | 8/2012 | Mayberry et al. |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,333,687 B2 | 12/2012 | Farnan et al. |
| 8,364,278 B2 | 1/2013 | Pianca et al. |
| 8,376,707 B2 | 2/2013 | McBride et al. |
| 8,388,565 B2 | 3/2013 | Shifflette et al. |
| 8,414,645 B2 | 4/2013 | Dwork et al. |
| 8,439,859 B2 | 5/2013 | Pfeffer et al. |
| 8,485,961 B2 | 7/2013 | Campbell et al. |
| 8,535,211 B2 | 9/2013 | Campbell et al. |
| 8,597,170 B2 | 12/2013 | Walters et al. |
| 8,608,635 B2 | 12/2013 | Yomtov et al. |
| 8,617,239 B2 | 12/2013 | Reitan |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,329 B2 | 6/2016 | Fitzgerald et al. |
| 9,358,330 B2 | 6/2016 | Schumacher |
| 2002/0010487 A1 | 1/2002 | Evans et al. |
| 2002/0047435 A1 | 4/2002 | Takahashi et al. |
| 2002/0094287 A1 | 7/2002 | Davis |
| 2002/0107506 A1 | 8/2002 | McGuckin et al. |
| 2002/0111663 A1 | 8/2002 | Dahl et al. |
| 2002/0151761 A1 | 10/2002 | Viole et al. |
| 2003/0018380 A1 | 1/2003 | Craig et al. |
| 2003/0023201 A1 | 1/2003 | Aboul-Hosn et al. |
| 2003/0100816 A1 | 5/2003 | Siess |
| 2003/0135086 A1 | 7/2003 | Khaw et al. |
| 2003/0187322 A1 | 10/2003 | Siess |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0010229 A1 | 1/2004 | Houde et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0116862 A1 | 6/2004 | Ray |
| 2004/0152944 A1 | 8/2004 | Medvedev et al. |
| 2004/0253129 A1 | 12/2004 | Sorensen et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |
| 2005/0113631 A1 | 5/2005 | Bolling et al. |
| 2005/0135942 A1 | 6/2005 | Wood et al. |
| 2005/0137680 A1 | 6/2005 | Ortiz et al. |
| 2005/0165269 A9 | 7/2005 | Aboul Hosn et al. |
| 2005/0165466 A1 | 7/2005 | Morris et al. |
| 2005/0250975 A1 | 11/2005 | Carrier et al. |
| 2005/0277912 A1 | 12/2005 | John |
| 2006/0005886 A1 | 1/2006 | Parrino et al. |
| 2006/0008349 A1 | 1/2006 | Khaw |
| 2006/0018943 A1 | 1/2006 | Bechert et al. |
| 2006/0036127 A1 | 2/2006 | Delgado, III et al. |
| 2006/0058869 A1 | 3/2006 | Olson et al. |
| 2006/0062672 A1 | 3/2006 | McBride et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0142785 A1 | 6/2007 | Lundgaard et al. |
| 2007/0156006 A1 | 7/2007 | Smith et al. |
| 2007/0203442 A1 | 8/2007 | Bechert et al. |
| 2007/0212240 A1 | 9/2007 | Voyeux et al. |
| 2007/0217932 A1 | 9/2007 | Voyeux et al. |
| 2007/0217933 A1 | 9/2007 | Haser et al. |
| 2007/0233270 A1 | 10/2007 | Weber et al. |
| 2007/0237739 A1 | 10/2007 | Doty |
| 2007/0248477 A1 | 10/2007 | Nazarifar et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0103442 A1 | 5/2008 | Kesten et al. |
| 2008/0103516 A1 | 5/2008 | Wulfman et al. |

(56) References Cited

U.S. PATENT DOCUMENTS

| | | |
|---|---|---|
| 2008/0103591 A1 | 5/2008 | Siess |
| 2008/0114339 A1 | 5/2008 | McBride et al. |
| 2008/0119943 A1 | 5/2008 | Armstrong et al. |
| 2008/0132748 A1 | 6/2008 | Shifflette |
| 2008/0167679 A1 | 7/2008 | Papp |
| 2008/0275290 A1 | 11/2008 | Viole et al. |
| 2008/0306327 A1 | 12/2008 | Shifflette |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0053085 A1 | 2/2009 | Thompson et al. |
| 2009/0062597 A1 | 3/2009 | Michael |
| 2009/0073037 A1 | 3/2009 | Penna et al. |
| 2009/0087325 A1 | 4/2009 | Voltenburg, Jr. et al. |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0030161 A1 | 2/2010 | Duffy |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0094089 A1 | 4/2010 | Litscher et al. |
| 2010/0127871 A1 | 5/2010 | Pontin |
| 2010/0137802 A1 | 6/2010 | Yodfat et al. |
| 2010/0174239 A1 | 7/2010 | Yodfat et al. |
| 2010/0191035 A1 | 7/2010 | Kang et al. |
| 2010/0197994 A1 | 8/2010 | Mehmanesh |
| 2010/0210895 A1 | 8/2010 | Aboul-Hosn et al. |
| 2010/0268017 A1 | 10/2010 | Siess et al. |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004046 A1 | 1/2011 | Campbell et al. |
| 2011/0004291 A1 | 1/2011 | Davis et al. |
| 2011/0009687 A1 | 1/2011 | Mohl |
| 2011/0015610 A1 | 1/2011 | Plahey et al. |
| 2011/0034874 A1 | 2/2011 | Reitan et al. |
| 2011/0071338 A1* | 3/2011 | McBride ............... F04D 29/528 600/16 |
| 2011/0076439 A1 | 3/2011 | Zeilon |
| 2011/0098805 A1 | 4/2011 | Dwork et al. |
| 2011/0106004 A1 | 5/2011 | Eubanks et al. |
| 2011/0152831 A1 | 6/2011 | Escudero et al. |
| 2011/0152906 A1 | 6/2011 | Escudero et al. |
| 2011/0152907 A1 | 6/2011 | Escudero et al. |
| 2011/0218516 A1 | 9/2011 | Grigorov |
| 2011/0237863 A1 | 9/2011 | Ricci et al. |
| 2011/0257462 A1 | 10/2011 | Rodefeld et al. |
| 2011/0270182 A1 | 11/2011 | Breznock et al. |
| 2011/0275884 A1 | 11/2011 | Scheckel |
| 2011/0300010 A1 | 12/2011 | Jarnagin et al. |
| 2012/0004495 A1 | 1/2012 | Bolling et al. |
| 2012/0029265 A1 | 2/2012 | LaRose et al. |
| 2012/0059213 A1 | 3/2012 | Spence et al. |
| 2012/0059460 A1 | 3/2012 | Reitan |
| 2012/0083740 A1 | 4/2012 | Chebator et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0220854 A1 | 8/2012 | Messerly et al. |
| 2012/0224970 A1 | 9/2012 | Schumacher et al. |
| 2012/0226097 A1 | 9/2012 | Smith et al. |
| 2012/0234411 A1 | 9/2012 | Scheckel et al. |
| 2012/0237357 A1 | 9/2012 | Schumacher et al. |
| 2012/0245404 A1 | 9/2012 | Smith et al. |
| 2012/0265002 A1 | 10/2012 | Roehn et al. |
| 2013/0041202 A1 | 2/2013 | Toellner et al. |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner et al. |
| 2013/0085319 A1 | 4/2013 | Evans et al. |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher et al. |
| 2013/0303831 A1 | 11/2013 | Evans et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0039465 A1 | 2/2014 | Heike et al. |
| 2014/0051908 A1 | 2/2014 | Khanal et al. |
| 2014/0067057 A1 | 3/2014 | Callaway et al. |
| 2014/0088455 A1 | 3/2014 | Christensen et al. |
| 2014/0148638 A1 | 5/2014 | LaRose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng |
| 2014/0301822 A1 | 10/2014 | Scheckel |
| 2014/0303596 A1 | 10/2014 | Schumacher et al. |
| 2015/0025558 A1 | 1/2015 | Wulfman et al. |
| 2015/0031936 A1 | 1/2015 | Larose et al. |
| 2015/0051435 A1 | 2/2015 | Siess et al. |
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher |
| 2016/0256620 A1 | 9/2016 | Scheckel et al. |

FOREIGN PATENT DOCUMENTS

| | | |
|---|---|---|
| EP | 0533432 A1 | 3/1993 |
| EP | 1207934 A2 | 5/2002 |
| EP | 1393762 A1 | 3/2004 |
| EP | 1591079 A1 | 11/2005 |
| EP | 2263732 A2 | 12/2010 |
| EP | 2298374 A1 | 3/2011 |
| EP | 2399639 A1 | 12/2011 |
| FR | 2267800 A1 | 11/1975 |
| GB | 2239675 A | 7/1991 |
| JP | S4823295 U | 3/1973 |
| JP | S58190448 A | 11/1983 |
| JP | H02211169 A | 8/1990 |
| JP | H06114101 A | 4/1994 |
| JP | H08196624 A | 8/1996 |
| JP | H1099447 A | 4/1998 |
| JP | 3208454 B2 | 9/2001 |
| TW | 500877 B2 | 9/2002 |
| WO | 1989005164 A1 | 6/1989 |
| WO | 9526695 A2 | 10/1995 |
| WO | 9715228 A1 | 5/1997 |
| WO | 1997037697 A1 | 10/1997 |
| WO | 2000012148 A2 | 3/2000 |

(56) References Cited

FOREIGN PATENT DOCUMENTS

| WO | 0019097 A1 | 4/2000 |
|---|---|---|
| WO | 0043062 A1 | 7/2000 |
| WO | 0069489 A1 | 11/2000 |
| WO | 2001017581 A2 | 3/2001 |
| WO | 0124867 A1 | 4/2001 |
| WO | 02070039 A2 | 9/2002 |
| WO | 03103745 A2 | 12/2003 |
| WO | 2005089674 A1 | 9/2005 |
| WO | 2005123158 A1 | 12/2005 |
| WO | 2009073037 A1 | 6/2009 |
| WO | 2009076460 A2 | 6/2009 |
| WO | 2010127871 A1 | 11/2010 |
| WO | 2010133567 A1 | 11/2010 |
| WO | 2010149393 A1 | 12/2010 |
| WO | 2011035926 A1 | 3/2011 |
| WO | 2011035929 A2 | 3/2011 |
| WO | 2011039091 A1 | 4/2011 |
| WO | 2011076439 A1 | 6/2011 |
| WO | 2011089022 A1 | 7/2011 |
| WO | 2012007140 A1 | 1/2012 |
| WO | 2012007141 A1 | 1/2012 |
| WO | 2013148697 A1 | 10/2013 |
| WO | 2013160407 A1 | 10/2013 |
| WO | 2014019274 A1 | 2/2014 |
| WO | 2015063277 A2 | 5/2015 |

OTHER PUBLICATIONS

International Search Report and Written Opinion received in International Patent Application No. PCT/US2015/045370, dated Feb. 25, 2016, in 10 pages.
International Search Report and Written Opinion received in International Patent Application No. PCT/US2016/014371, dated Jul. 28, 2016, in 16 pages.
International Search Report and Written Opinion received in International Patent Application No. PCT/US2016/014379, dated Jul. 29, 2016, in 17 pages.
International Search Report and Written Opinion received in International Patent Application No. PCT/US2016/014391, dated Jul. 28, 2016, in 15 pages.
International Search Report and Written Opinion received in International Patent Application No. PCT/US2016/051553, dated Mar. 23, 2017, in 11 pages.
International Search Report received in International Patent Application No. PCT/US2003/004401, dated Jan. 22, 2004, in 7 pages.
International Search Report received in International Patent Application No. PCT/US2003/004853, dated Nov. 10, 2003, in 5 pages.
JOMED Reitan Catheter Pump RCP, Feb. 18, 2003, in 4 pages.
JOMED Reitan Catheter Pump RCP, Percutaneous Circulatory Support, in 10 pages, believed to be published prior to Oct. 15, 2003.
Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist JOMED Catheter PumpTM, in 6 pages, believed to be published prior to Jun. 16, 1999.
Morgan, "Medical Shape Memory Alloy Applications-The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD,"The International Journal of Artificial Organs, 1997, pp. 277-284; vol. 20(5).

Nishimura et al., "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Reitan, Evaluation of a New Percutaneous Cardiac Assist Device, Department of Cardiology, Faculty of Medicine, Lund University, Sweden, 2002, in 172 pages.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al., "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Siess et al., "Basic design criteria for rotary blood pumps," H. Masuda, Rotary Blood Pumps, Springer, Japan, 2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Arlilicial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Sieß et al., "Hydraulic refinement of an intraarterial microaxial blood pump", The International Journal of Artificial Organs, 1995, vol. 18, No. 5, pp. 273-285.
Sieß, "Systemanalyse und Entwicklung intravasaler Rotationspumpen zur Herzunterstutzung", Helmholtz-Institut fur Blomedixinische Technik an der RWTH Aachen, Jun. 24, 1998, in 105 pages.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.
Supplemental European Search Report received from the European Patent Office in EP Application No. EP 05799883 dated Mar. 19, 2010, 3 pages.

(56) References Cited

OTHER PUBLICATIONS

Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Wampler et al., "The Sternotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Written Opinion received in International Patent Application No. PCT/US2003/04853, dated Feb. 25, 2004, 5 pages.
"Statistical Analysis and Clinical Experience with the Recover® Pump Systems", Impella CardioSystems GmbH, Sep. 2005, 2 sheets.
Abiomed—Recovering Hearts. Saving Lives , Impella 2 5 System, Instructions for Use, Jul. 2007, in 86 sheets.
Abiomed, "Impella 5.0 with the Impella Console, Circulatory Support System, Instructions for Use & Clinical Reference Manual," Jun. 2010, in 122 pages.
Aboul-Hosn et al., "The Hemopump: Clinical Results and Future Applications", Assisted Circulation 4, 1995, in 14 pages.
Barras et al., "Nitinol-lts Use in Vascular Surgery and Other Applications," Eur. J. Vase. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the HEMOPUMP Temporary Cardiac Assist System, Johnson & Johnson Interventional Systems, 1988, in 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, pp. 149-160; vol. A273.
European Search Report received in European Patent Application No. 05799883.3, dated May 10, 2011, in 4 pages.
Extended EP Search Report, dated Mar. 15, 2018, for related EP patent application No. EP 15833166.0, in 7 pages.
Extended European Search Report received in European Patent Application No. 07753903.9, dated Oct. 8, 2012, in 7 pages.
Extended European Search Report received in European Patent Application No. 13790890.1, dated Jan. 7, 2016, in 6 pages.
Extended European Search Report received in European Patent Application No. 13791118.6, dated Jan. 7, 2016, in 6 pages.
Extended European Search Report received in European Patent Application No. 13813687.4, dated Feb. 24, 2016, in 6 pages.
Extended European Search Report received in European Patent Application No. 13813867.2, dated Feb. 26, 2016, in 7 pages.
Extended European Search Report received in European Patent Application No. 14764392.8, dated Oct. 27, 2016, in 7 pages.
Extended European Search Report received in European Patent Application No. 14779928.2, dated Oct. 7, 2016, in 7 pages.
Federal and Drug Administration 510(k) Summary for Predicate Device IMPELLA 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device—the Integrated Cardioassist Catheter—in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
International Preliminary Examination Report received in International Patent Application No. PCT/US2003/04401, dated May 18, 2004, in 4 pages.
International Preliminary Examination Report received in International Patent Application No. PCT/US2003/04853, dated Jul. 26, 2004, in 5 pages.
International Preliminary Report on Patentability and Written Opinion of the International Searching Authority received in International Patent Application No. PCT/US2005/033416, dated Mar. 20, 2007, in 7 pages.
International Preliminary Report on Patentability and Written Opinion of the International Searching Authority received in International Patent Application No. PCT/US2007/007313, dated Sep. 23, 2008, in 6 pages.
International Preliminary Report on Patentability and Written Opinion received in International Patent Application No. PCT/US2014/020878, dated Sep. 15, 2015, in 8 pages.
International Search Report and Written Opinion received in International Patent Application No. PCT/US2005/033416, dated Dec. 11, 2006, in 8 pages.
International Search Report and Written Opinion received in International Patent Application No. PCT/US2007/007313, dated Mar. 4, 2008, in 6 pages.
International Search Report and Written Opinion received in International Patent Application No. PCT/US2010/040847, dated Jan. 6, 2011, in 15 pages.
International Search Report and Written Opinion received in International Patent Application No. PCT/US2012/020369, dated Jul. 30, 2012, in 10 pages.
International Search Report and Written Opinion received in International Patent Application No. PCT/US2012/020382, dated Jul. 31, 2012, in 11 pages.
International Search Report and Written Opinion received in International Patent Application No. PCT/US2012/020383, dated Aug. 17, 2012; in 9 pages.
International Search Report and Written Opinion received in International Patent Application No. PCT/US2012/020553, dated Aug. 17, 2012, in 8 pages.
International Search Report and Written Opinion received in International Patent Application No. PCT/US2013/040798, dated Aug. 21, 2013, in 16 pages.
International Search Report and Written Opinion received in International Patent Application No. PCT/US2013/040799, dated Aug. 21, 2013, in 19 pages.
International Search Report and Written Opinion received in International Patent Application No. PCT/US2013/040809, dated Sep. 2, 2013, in 25 pages.

(56) References Cited

OTHER PUBLICATIONS

International Search Report and Written Opinion received in International Patent Application No. PCT/US2013/048332, dated Oct. 16, 2013, in 14 pages.
International Search Report and Written Opinion received in International Patent Application No. PCT/US2013/048343, dated Oct. 11, 2013, in 15 pages.
International Search Report and Written Opinion received in International Patent Application No. PCT/US2014/020790, dated Oct. 9, 2014, in 9 pages.
International Search Report and Written Opinion received in International Patent Application No. PCT/US2014/020878, dated May 7, 2014, in 11 pages.
International Search Report and Written Opinion received in International Patent Application No. PCT/US2015/025959, dated Oct. 22, 2015, in 9 pages.
International Search Report and Written Opinion received in International Patent Application No. PCT/US2015/025960, dated Oct. 22, 2015, in 11 pages.
International Search Report and Written Opinion received in International Patent Application No. PCT/US2015/026013, dated Oct. 22, 2015, in 8 pages.
International Search Report and Written Opinion received in International Patent Application No. PCT/US2015/026014, dated Oct. 22, 2015, in 8 pages.

* cited by examiner

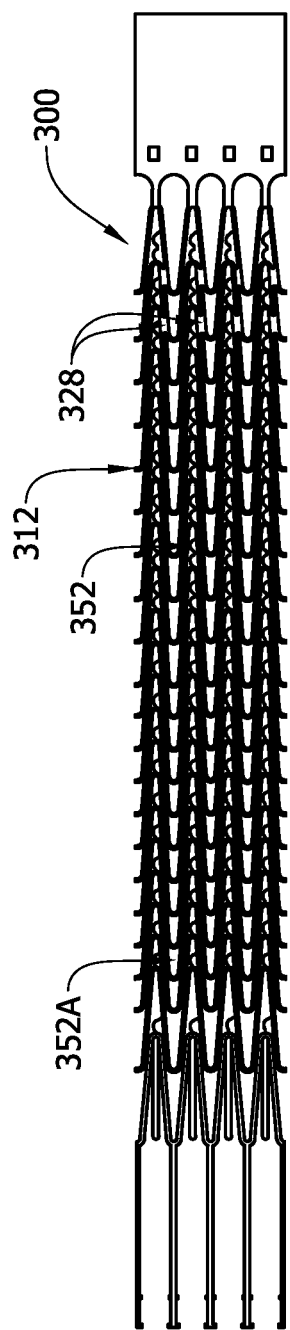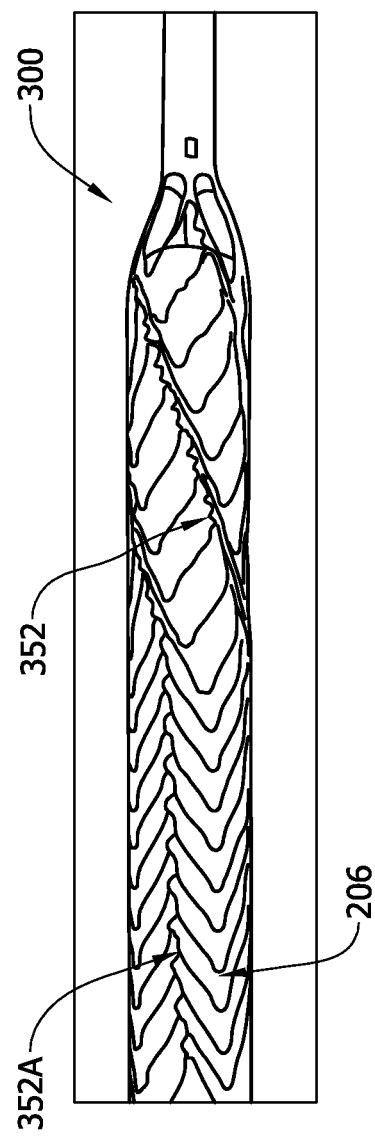
FIGURE 8
FIGURE 9

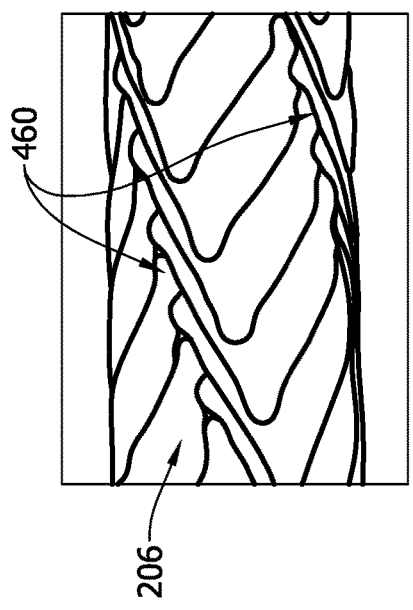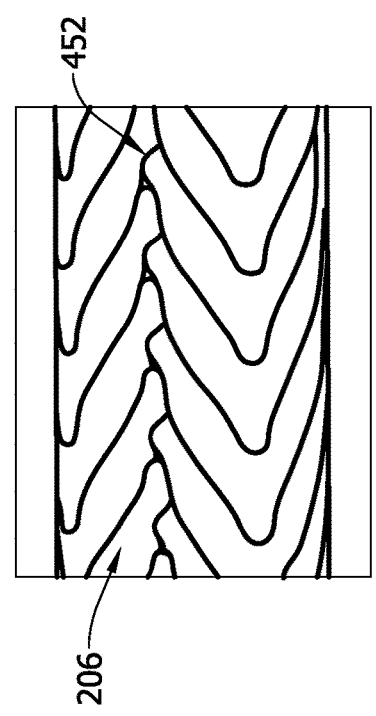

CATHETER PUMP

CROSS REFERENCE TO RELATED APPLICATIONS

This application is a continuation of U.S. patent application Ser. No. 16/110,648, filed Aug. 23, 2018, entitled, "CATHETER PUMP," now U.S. Pat. No. 11,058,865, which is a divisional of U.S. patent application Ser. No. 15/172,664, filed June 3, 2016, entitled "CATHETER PUMP," now U.S. Pat. No. 10,086,121, which is a divisional of U.S. patent application Ser. No. 13/801,528, filed Mar. 13, 2013, entitled "CATHETER PUMP," now U.S. Pat. No. 9,358,329, which claims priority to U.S. Provisional Patent Application No. 61/667,903 filed Jul. 3, 2012, entitled "CATHETER PUMP," all of which are hereby incorporated by reference in their entirety.

BACKGROUND OF THE INVENTION

Field of the Invention

This application is directed to a catheter pump for mechanical circulatory support of a heart.

Description of the Related Art

Heart disease is a major health problem that has high mortality rate. After a heart attack, only a small number of patients can be treated with medicines or other non-invasive treatment. However, a significant number of patients can recover from a heart attack or cardiogenic shock if provided with mechanical circulatory support.

In a conventional approach, a blood pump having a fixed cross-section is surgically inserted between the left ventricle and the aortic arch to assist the pumping function of the heart. Other known applications involve providing for pumping venous blood from the right ventricle to the pulmonary artery for support of the right side of the heart. The object of the surgically inserted pump is to reduce the load on the heart muscle for a period of time, to stabilize the patient prior to heart transplant or for continuing support. Surgical insertion, however, can cause additional serious stresses in heart failure patients.

Percutaneous insertion of a left ventricular assist device ("LVAD"), a right ventricular assist device ("RVAD") or in some cases a system for both sides of the heart (sometimes called biVAD) therefore is desired. Conventional fixed cross-section ventricular assist devices designed to provide near full heart flow rate are too large to be advanced percutaneously, e.g., through the femoral artery.

There is a continuing need for improved cannula that provide sufficient expansion force and a stable expanded shape while still allowing for reliable and easy collapse to a delivery size. In other words, the cannula should have sufficient force to expand, but also be collapsible under significant sheathing force while avoiding a risk of damaging the cannula during re-sheathing. There is a continuing need for improved cannula that can be expanded and collapsed, in some cases over many cycles, without risking breakage of the struts and connectors forming the mesh. Broken struts pose a risk of complicating patient treatment and/or compromising the performance of the device.

SUMMARY OF THE INVENTION

There is an urgent need for a pumping device that can be inserted percutaneously and also provide full cardiac rate flows of the left, right, or both the left and right sides of the heart when called for.

In one embodiment, an apparatus is provided for inducing motion of a fluid relative to the apparatus. The apparatus can be a catheter pump, as discussed below. The apparatus can include a rotatable impeller and an elongate cannula. The cannula has a plurality of circumferential members and a plurality of circumferential connectors. The circumferential members are disposed about a space, e.g., a volume including at least the impeller zone. One or more of, e.g., each of, the circumferential members can have an undulating configuration including a plurality of apices connected by elongate struts. The circumferential connectors can be disposed between alternating struts of adjacent circumferential members. A plurality of axial connectors is disposed between a proximal side of a proximal apex and a distal side of an adjacent circumferential member in the impeller zone of cannula.

In some embodiments, the cannnula is differentiated along its length to have varying stiffness. The elongate cannula has an impeller zone disposed about the impeller and a distal zone disposed distal of the impeller zone. The distal zone can be made more flexible by reducing the number of connectors disposed therein. For example, the impeller zone can have alternating elongate struts that are connected by circumferential connectors and the distal zone can have alternating elongate struts that are free of such connections.

In one variation, each of the connectors of the plurality has a distal end coupled with a proximal side of a proximal apex of a first circumferential member, a proximal end coupled with a distal face of a second circumferential member disposed adjacent to and proximal of the first circumferential member. Each of the connectors has an arcuate section disposed between the proximal and distal ends. In this variation, the arcuate section comprises a single convex portion disposed between the proximal and distal ends.

A first plurality of axial connectors is disposed between a proximal side of a proximal apex and a distal side of an adjacent circumferential member in the impeller zone of the cannula. A second plurality of axial connectors is disposed between a proximal side of a proximal apex and a distal side of an adjacent circumferential member in the distal zone of the cannula.

In another embodiment, an apparatus for pumping blood includes a rotatable impeller, an elongate cannula, and a sheath configured to be positioned over the elongate cannula. The elongate cannula has a plurality of circumferential members disposed about the impeller. One or more of, e.g., each of, the circumferential members can have an undulating configuration. The undulating configuration can include a plurality of proximal and distal apices, with proximal apices connected to distal apices by an elongate strut. The sheath is configured to be positioned over the elongate cannula to actuate the cannula from an expanded configuration to a collapsed configuration. The elongate cannula is configured to deflect radially inwardly in an area around the proximal apices before the apices move into the sheath.

In some configurations, the elongate cannula has an impeller zone disposed about the impeller and a distal zone disposed distal of the impeller zone. For example, the impeller can extend in about one-half or less of the length of the cannula. The distal zone may be more easily compressed by the sheath because the impeller is not present in that area. As a result, the cannula can have a different configuration in the distal zone.

In another configuration, a catheter pump is provided. A catheter pump is an example of an apparatus for inducing motion of a fluid relative to the apparatus. The catheter pump includes a rotatable impeller and an elongate cannula having a mesh comprising a plurality of circumferential members disposed about the impeller. The mesh also has a plurality of axial connectors extending between a proximal side of a distal circumferential member and a distal side of a proximal circumferential member. The circumferential members are radially self-expandable. A sheath is configured to be positioned over the elongated cannula to actuate the cannula from an expanded configuration to a collapsed configuration. The cannula is configured to minimize a risk of fracture within the mesh, e.g., of the axial connectors, as the elongated cannula moves into the sheath.

In a further embodiment, an apparatus for inducing motion of a fluid relative to the apparatus is provided. The apparatus includes a a rotatable impeller and an elongate cannula. The elongate cannula is defines a blood flow channel in which the impeller is disposed. The cannula has an expandable structure comprising that has a plurality of circumferential members, a plurality of circumferential connectors, and a plurality of axial connectors. The circumferential members are disposed about the blood flow channel. The circumferential members have an undulating configuration including a plurality of apices connected by elongate struts. The circumferential connectors are disposed between alternating struts of adjacent circumferential members. The axial connectors have a distal end coupled with a proximal side of a proximal apex of a first circumferential member, a proximal end coupled with a distal face (e.g., an edge) of a second circumferential member disposed adjacent to and proximal of the first circumferential member. The axial connectors have an arcuate section disposed between the proximal and distal ends. The arcuate section comprises a single convex portion disposed between the proximal and distal ends.

In another embodiment, an apparatus for pumping blood is provided that includes a rotatable impeller, an elongate cannula, and an axial member. The elongate cannula has a plurality of circumferential members disposed about the impeller. One or more of the circumferential members has an undulating configuration including a plurality of proximal and distal apices. Each proximal apex is connected to a distal apex by an elongate strut. The axial member has a distal end coupled with a proximal apex of a first circumferential member a proximal end coupled with a second circumferential member disposed proximal of the first circumferential member. The axial member has a length that is less than the distance between the proximal apex to which the distal end of the axial member is connected and a proximal apex of the second circumferential member that is axially aligned with the proximal apex to which the distal end of the axial member is connected.

In another embodiment, a catheter pump is provided that includes a rotatable impeller and an elongate cannula. The elongate cannula has a mesh that has a plurality of circumferential members disposed about the impeller. The elongate cannula has a plurality of axial connector extending between a proximal side of a distal circumferential member and a distal side of a proximal circumferential member. The circumferential members are radially self-expandable. The cannula is configured to minimize fracture within at least in the distal zone of the mesh as the elongated cannula moves into a sheathing device.

In another embodiment, a cannula for conveying blood is provided that includes an in-situ expandable and collapsible mesh structure and a polymeric enclosure. The in-situ expandable and collapsible mesh structure has a plurality of undulating circumferential members surrounding a lumen. Each circumferential member has proximal and distal vertices. The polymeric enclosure is disposed about the mesh structure to enclose the lumen along a length between an inlet and an outlet. The number of proximal vertices in an area defined between a proximal circumference intersecting the proximal vertex of a circumferential member and a distal circumference intersecting the distal vertex of the same circumferential member adjacent to the proximal vertex is at least two.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 4A is a detail view of a distal portion of the wall pattern of FIG. 4;

FIG. 8 illustrates another wall pattern of a mesh structure in a flat configuration, where the mesh structure is configured to provide enhanced flexibility in a distal zone, while minimizing fracture risk;

FIG. 9 shows a formed mesh structure for a cannula having the wall pattern of FIG. 8;

FIG. 13 is a detail view of a first variation of the distal portion of the formed mesh structure of FIG. 12;

FIG. 14 is a detail view of a second variation of the distal portion of the formed mesh structure of FIG. 12;

FIG. 14A-1 is a detail view of a proximal portion of another variation of a wall pattern that is stable and minimizes fracture;

FIG. 14A-2 is a detail view of a central portion of the wall pattern for which the proximal portion is shown in FIG. 14A-1

FIG. 14A-3 is a detail view of a distal portion of the wall pattern for which the proximal portion is shown in FIG. 14A-1

More detailed descriptions of various embodiments of components for heart pumps useful to treat patients experiencing cardiac stress, including acute heart failure, are set forth below.

DETAILED DESCRIPTION OF THE PREFERRED EMBODIMENT

This application is directed to apparatuses for inducing motion of a fluid relative to the apparatus. The apparatus can be a catheter pump, e.g., a percutaneous heart pump.

Figure 1:
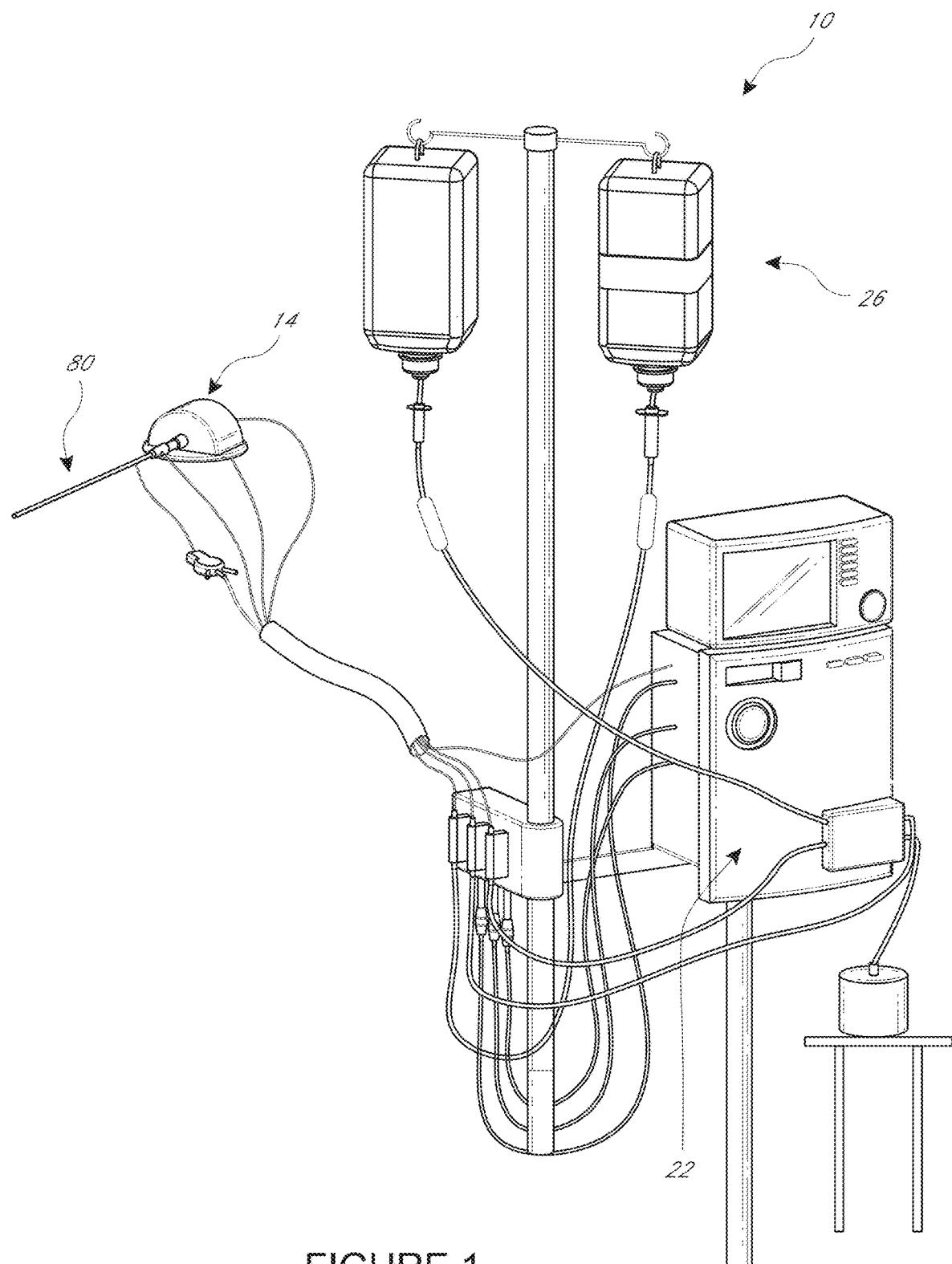
FIG. 1 illustrates one embodiment of a catheter pump configured for percutaneous application and operation.
Figure 2:
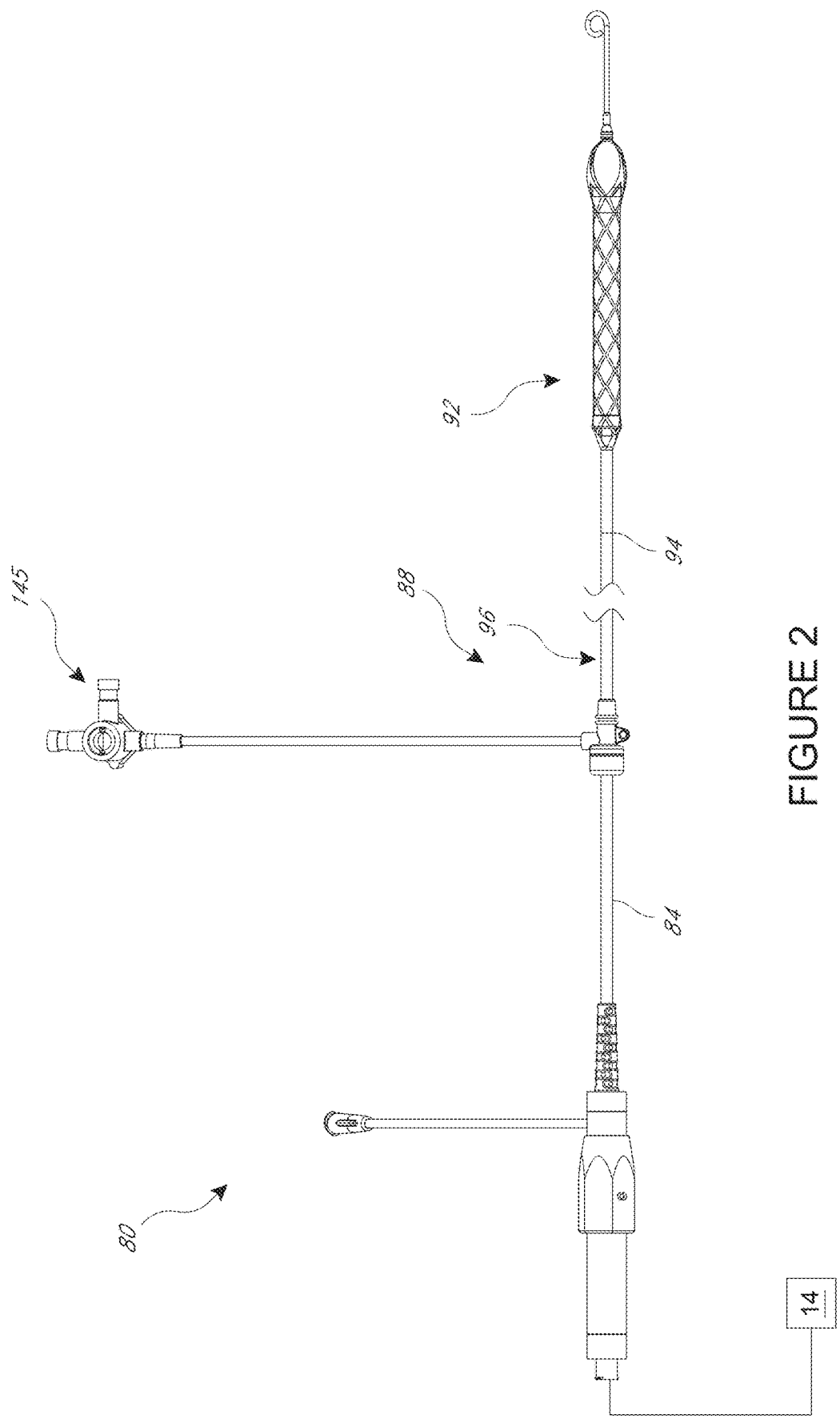
FIG. 2 is a plan view of one embodiment of a catheter assembly adapted to be used with the catheter pump of FIG. 1.

FIGS. 1 and 2 illustrate various features of a catheter pump 10. The catheter pump 10 can provide high performance including flow rates similar to full cardiac output. The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. In various embodiments, the impeller is rotated remotely by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178,922; and 6,176,848, all of which are hereby incorporated by reference herein in their entirety for all purposes.

Figure 3:
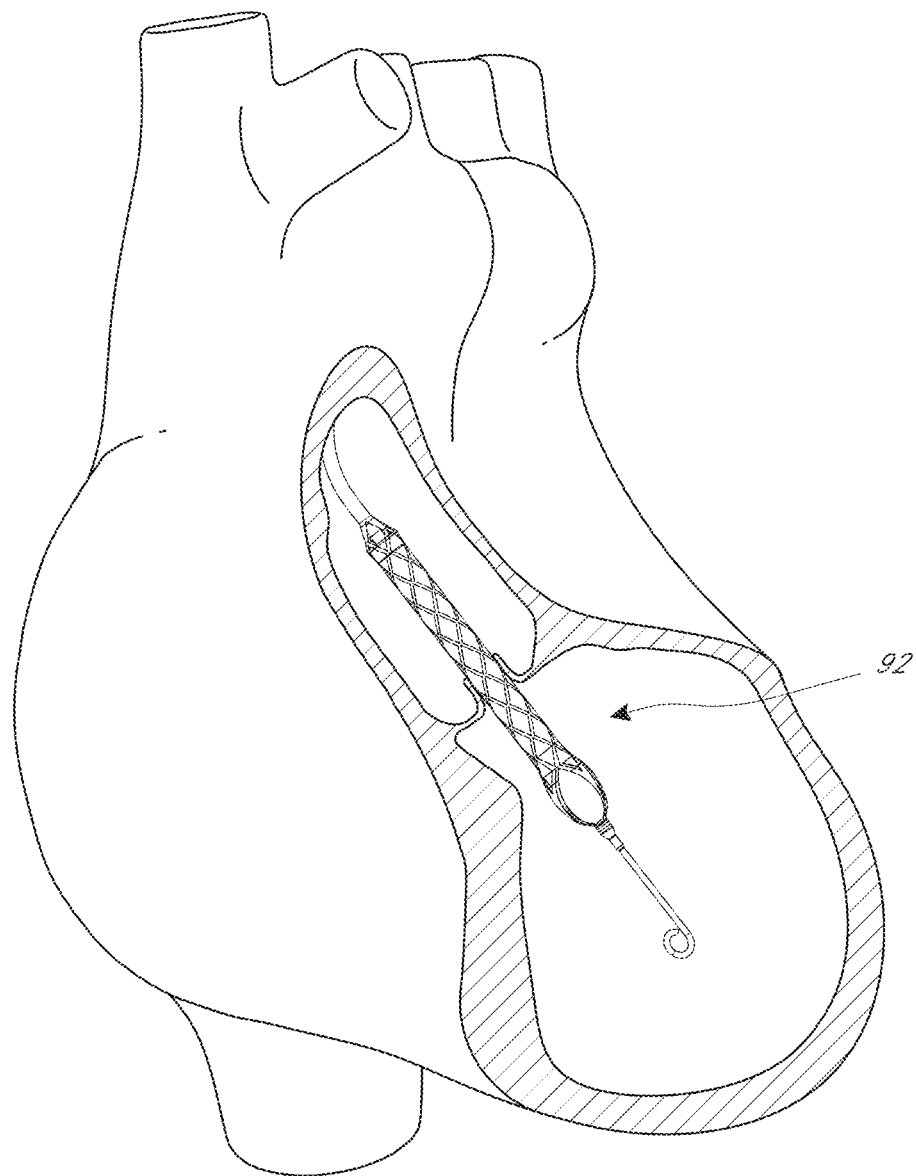
FIG. 3 show a distal portion of the catheter assembly of similar to that of FIG. 2 in position within the anatomy.

FIG. 3 illustrates one use of the catheter pump 10. A distal portion of the pump 10 is placed in the left ventricle LV of the heart to pump blood from the LV into the aorta. The pump 10 can be used in this way to treat patients with a wide range of conditions, including cardiogenic shock, myocardial infarction, and acutely decompensated heart failure, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and U.S. patent application Ser. No. 2012-0203056A1, all of which are hereby incorporated by reference herein in their entirety for all purposes.

FIG. 2 shows features that facilitate small blood vessel percutaneous delivery and high performance up to and in some cases exceeding normal cardiac output in all phases of the cardiac cycle. In particular, the catheter system 80 includes a catheter body 84 and a sheath assembly 88. An impeller assembly 92 is coupled with the distal end of the catheter body 84. The impeller assembly 92 is expandable and collapsible. In the collapsed state, the distal end of the catheter system 80 can be advanced to the heart. In the expanded state the impeller assembly 92 is able to pump blood at relatively high flow rates. FIGS. 2 and 3 illustrate the expanded state. The collapsed state can be provided by advancing a distal end 94 of an elongate body 96 distally over the impeller assembly 92 to cause the impeller assembly 92 to collapse. This provides an outer profile throughout the catheter assembly 80 that is of small diameter, for example 12.5 French as discussed further below.

Embodiments of the catheter pumps of this application can be configured with expandable structures to enhance performance. For example, an impeller for moving blood axially can be provided. The impeller can be positioned in an expandable cannula. When so positioned, the expandable cannula provides dual function of enclosing a blood flow lumen through which the impeller can act and also housing the impeller. In that sense, the cannula is also an expandable housing. The expandable cannula and impeller provide a flow rate in the pump that is much larger than would be possible using percutaneous access techniques were these components not capable of expanding. However, it may be possible to reduce flow resistance by increasing the size of a blood-flow cannula even with a fixed diameter impeller. Also, it may be possible to sequentially collapse the impeller, e.g., by withdrawing the impeller into a rigid ring or tubular segment prior to collapsing the impeller. These variant also benefit from many of the embodiments herein and are within the scope of this application even though the impeller may not be housed in the cannula at all times or at all.

While these configurations provide excellent flow rates, a challenge arises in collapsing the expanded structures prior to removal from the patient. The collapsing of the impeller assembly 92 is this manner is not straight-forward. In various embodiments, a mesh is used to support the expandable portion of a blood flow conduit in the impeller assembly 92. The expandable portion can include a self-expanding structure that expands when undulating generally ring-shaped members release stored strain energy arising from circumferential compression. Compression of such a structure involves transforming axial relative movement of the sheath assembly 88 over the catheter body 84 into a circumferential compression force. There is a chance that such movement will cause the distal end to become lodged between adjacent undulating members. Such problems with compression can be more likely to occur when the undulating members are spaced apart by an axial distance that is greater than the wall thickness of the distal end of the sheath assembly 88. While the undulating members could be moved much closer together, such an approach could make the expandable structure too stiff thereby inhibiting collapse of the expandable portion. Some embodiments herein are configured to reduce this risk, while retaining sufficient flexibility. Some embodiments are configured to prevent connectors between adjacent rings from being deformed around the distal end of the sheath assembly 88. Various aspects of the expandable cannula and/or mesh in accordance with the invention achieve a careful balance of expansion force, collapsing force, and structural strength. FIGS. 4-16 illustrate various embodiments of mesh structures that can be incorporated into the expandable cannula to provide advantageous performance in use.

Additional details of the structures disclosed in these figures, and various modified embodiments thereof, and method related to the same are discussed in U.S. patent application Ser. No. 13/343,617, filed Jan. 4, 2012, now U.S. Pat. 8,485,961, which is hereby incorporated by reference herein in its entirety. In addition, this application incorporates by reference in its entirety and for all purposes the subject matter disclosed in each of the following concurrently filed applications: U.S. patent application Ser. No. 13/802,556, entitled "DISTAL BEARING SUPPORT," now U.S. Pat. No. 9,446,179, filed Nov. 14, 2013; U.S. Provisional Patent Application No. 61/780,656, entitled "FLUID HANDLING SYSTEM," filed; U.S. patent application Ser. No. 13/801,833, entitled "SHEATH SYSTEM FOR CATHETER PUMP," now U.S. Pat. No. 9,872,947, filed Jan. 23, 2018; U.S. patent application Ser. No. 13/802,570, entitled "IMPELLER FOR CATHETER PUMP," now U.S. Pat. No. 8,721,517, filed May 13, 2014; and U.S. patent application Ser. No. 13/802,468, entitled "MOTOR ASSEMBLY FOR CATHETER PUMP," now U.S. Pat. No. 9,421,311, filed Aug. 23, 2016.

Figure 4:
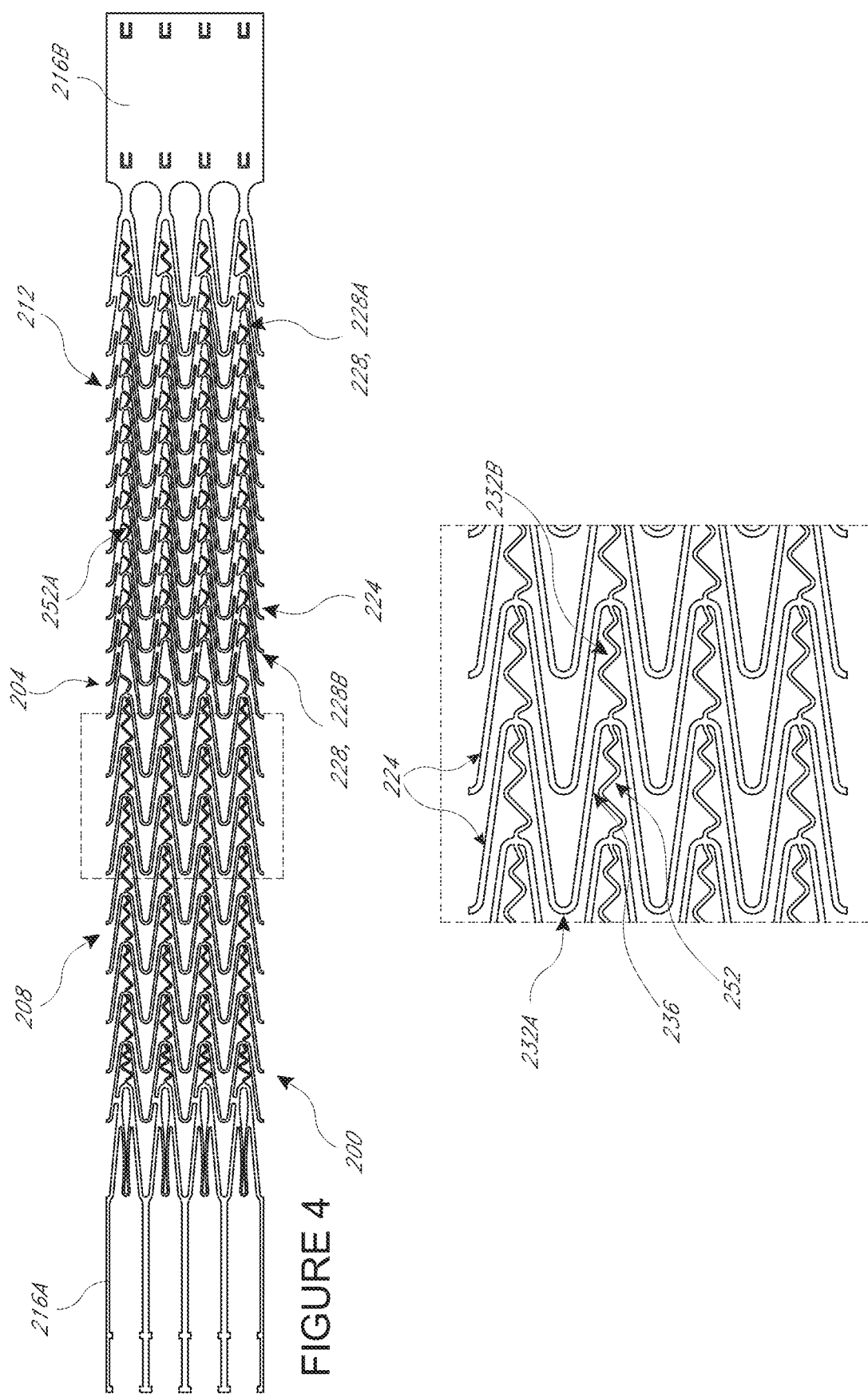
FIG. 4 illustrates a wall pattern of a mesh structure in a flat configuration, where the mesh structure is configured to provide enhanced flexibility in a distal zone.

FIG. 4 shows a flat wall pattern 200 of a mesh structure 204 that is configured to provide enhanced flexibility in a distal zone 208. The distal zone 208 is disposed distally of an impeller zone 212, which is a portion of the mesh structure 204 that is disposed around an impeller in the catheter assembly of FIG. 2. The impeller can be part of the impeller assembly 116, as set forth in more detail in the U.S. patent application Ser. No. 13/343,617, now U.S. Pat. No. 8,485,961, incorporated by reference above. In some embodiments, the distal zone 208 and the impeller zone 212 are distinct from each other, for example having separate structure or performance characteristics. In other embodiments, the distal and impeller zones 208, 212 are general regions of an otherwise continuous structure. In some embodiments, the distal and impeller zones overlap. The wall pattern 200 also includes distal and proximal end connection structures 216A, 216B, which are discussed in detail in the '617 application incorporated by reference above, and also in U.S. patent application Ser. No. 13/343,618, filed Dec. 3, 2013, entitled "CATHETER PUMP," now U.S. Pat. No. 8,597,170, which is hereby incorporated by reference herein in its entirety.

The wall pattern 200 illustrates a plurality of circumferential members 224 and a plurality of circumferential connectors 228. In the flat view of FIGS. 4 and 4A, the circumferential members 224 can be seen to extend transversely to a longitudinal axis of the pattern 200. In the formed view of FIGS. 5 and 5A, these structures can be seen to extend about the circumference of the formed mesh structure 204. As discussed below, e.g., in connection with FIGS. 7 and 7A, a cannula is formed by enclosing the circumferential members 224 with a polymer material 206, e.g., a film, to create a flow channel open on the ends but otherwise sealed to maximize axial flow through the cannula and the pump. Thus, the circumferential members 224 and later the cannula are disposed about a space, e.g., a volume including at least the impeller zone 212.

In various embodiments, the polymer material 206 is a coating disposed about the cannula mesh structure 204. Suitable materials for the polymer coating include, but are not limited to a biocompatible polymer, a drug-eluting polymer, and a functionalized polymer such as a thrombo-resistant material. In various embodiments, the polymer material 206 is Hapflex™ or Thoralon™. In the exemplary structure, the polymer material 206 fills the voids in the mesh structure. The polymer material 206 also coats the inner and outer walls such that the mesh structure does not come into contact with blood and tissue. In various embodiments, the polymer material 206 is a thin coating. In various embodiments, the polymer coating 206 has a maximum thickness of less than 10 microns, less than 9 microns, less than 8 microns, less than 7 microns, less than 6 microns, less than 5 microns, less than 4 microns, less than 3 microns, less than 2 microns, or less than 1 micron. In various embodiments, the polymer coating 206 is formed of a plurality of layers. In various embodiments, the polymer coating 206 is configured to reinforce the mesh structure. The polymer material 206 may be applied by dip coating, molding, spinning on a mandrel, or other techniques. One will appreciate from the description herein that the polymer coating 206 may be configured and applied in various other manners. Further details of suitable materials are set forth in U.S. Pat. Nos. 4,675,361 and 6,939,377, which are incorporated by reference herein in their entireties and for all purposes.

The circumferential members 224 preferably are configured to be self-expandable, also described as self-expanding herein. FIG. 4 shows that in one embodiment one or more of the circumferential members 224 can have an undulating configuration. As can be seen in many of the figures, and in FIG. 4A specifically, circumferential members can have an alternating structure, e.g., a plurality proximal turns and distal turns connected by struts. The struts can be straight members that each have a proximal ends connected to a proximal turn and a distal end connected to a distal turn. The distal turns can be peaks and the proximal turns can be valleys, e.g., if the cannula is held with the distal end up. The distal turns can be crests and the proximal turns can be troughs, e.g., if the cannula is held with the distal end up. In some cases, the circumferential members have a generally serpentine configuration, or can be sinusoidal in nature disposed on both sides of a transverse plane. The circumferential members 224 can include a plurality of distal and proximal apices 232A, 232B connected by elongate struts 236. As discussed further below, the density of the circumferential members 224 can be varied to modify the performance or the cannula.

The circumferential connectors 228 can be disposed between alternating struts 236 of adjacent circumferential members 224 in at least one of the distal and impeller zones 208, 212. For example, the connectors 228 (or other connectors discussed herein) can join a node on one circumferential member to a node on an adjacent circumferential member. In the case of the connectors 228, the nodes are offset from the peaks and valleys. At least one of the nodes can be disposed on a strut that extends between adjacent nodes. In some cases, connectors are disposed between the crests and trough and can be disposed between a crest the a transverse mid-point of a sinusoidal circumferential member. In some patterns, the width of nodes are greater in the impeller zone than distal thereof. FIG. 4 shows that circumferential connector 228 can be provided between opposing sides of adjacent struts 236 of at least two adjacent circumferential members 224 in the impeller zone. In one embodiment, alternating elongate struts 236 are connected to an adjacent elongate strut of an adjacent circumferential member 224. In one embodiment, alternating elongate struts 236 are not connected to adjacent elongate struts by circumferential connectors 228. The elongate struts 236 that are not connected by circumferential connectors 228 are able to expand to a greater degree, providing for asymmetrical expansion about an apex in some embodiments. In this context, asymmetrical can refer to unequal movement upon expansion of the elongate struts 236 away from a central axis extending through an unexpanded apex. The central axis can be an axis intersecting an apex and being located equal distance from inner edges of unexpanded adjacent elongate struts 236.

FIG. 4 shows that while circumferential connectors 228 are provided in the impeller zone 212, the connectors 228 can be omitted in the distal zone 208. Such an arrangement provides enhanced rigidity of the impeller zone 212 compared to the distal zone 208. FIGS. 6 and 14A-1 to 14A-3 are other embodiments in which circumferential connectors 228 are provide throughout a distal zone as well as in an impeller zone. More generally, the circumferential connectors 228 can be provided between opposing sides of alternating adjacent elongate struts of less than all of the circumferential members in the distal zone 208, while still providing benefits as discussed below. For example, a substantial portion such as one-half or more of the struts 236 can be connected by circumferential connectors 228 in the distal portion in one embodiment. In some embodiments, the density of connectors 228 in the distal zone 208 can be about one-half or less that in the impeller zone 212.

In various embodiments, there can be different groups of circumferential connectors 228. For example, in FIG. 4 two groups of circumferential connectors 228A, 228B can be provided. A first plurality connectors 228A can be provided about the impeller zone 212 in which the connectors have a length along the struts 236 that the connectors 228A join that is greater than the separation between adjacent circumferential members, e.g. between the struts 236 that they join. The length of the connectors 228A along the struts 236 that they join is greater than the separation between adjacent circumferential members in the unexpanded state in some embodiments. A second plurality connectors 228B can be provided between the impeller an distal zones 212, 208 in which the connectors have a length along the struts 236 that they join that is less than the length of the connectors 228A. For example, the length of each of the connectors 228B along the struts 236 to which they are coupled can be about one-half that of the first connectors 228A. By providing longer connectors 228A, enhanced stiffness can be provided in the impeller zone 212. This can aid in collapsing the cannula, as discussed below. Longer connectors 228A also contributes to dimensional stability of the impeller zone 212, e.g., to minimize variance of a gap between a tip of an impeller and an inner surface of the cannula in the impeller zone 212.

FIG. 4A shows details of a portion of the distal zone 208. For example, a plurality of axial connectors 252 can be provided between proximal side of a proximal apex and a distal side of an adjacent circumferential member in the distal zone of the cannula. The same connectors can be provided in the impeller zone 212. FIG. 4 shows that in some embodiments a modified axial connector 252A can be provided in the impeller zone 212. The connectors 252A have a first end that forms an apical connection with a proximally oriented apex 232B and a second end. The second end is coupled in between adjacent apices of a circumferential member, e.g., along a side of an elongate strut 236. The connectors 252A can be connected to the struts 236 at the same location that the strut connects to an adjacent strut by way of the connector 228A. The connectors 252A are shortened compared to the connectors 252. For example, they can extend with fewer undulations along their length, e.g., with a single inflection point between the ends.

Figure 5:
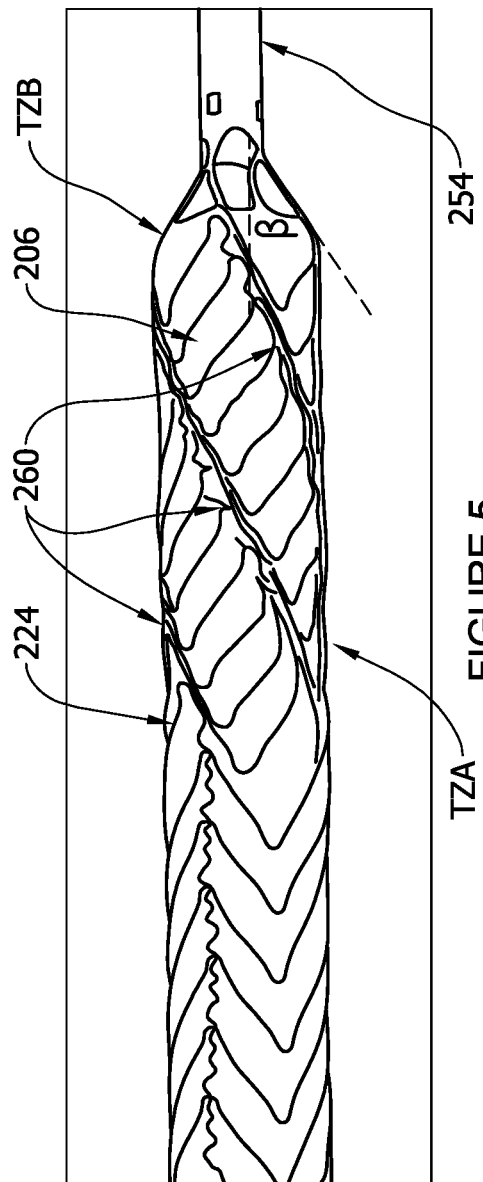
FIG. 5 shows a formed mesh structure for a cannula having a wall pattern similar to that of FIG. 4.

In one embodiment, substantially all of the impeller zone 212 has enhanced rigidity connectors 252A. FIG. 5 shows a transition zone that can be provided at one or both of the proximal and distal ends of the impeller zone 212. For example, a transition zone TZ-B can be provided to facilitate radial transition from the expanded size of the formed mesh to the diameter of a non-expanding portion 254 of the formed mesh that does not expand. A transition zone TZ-A between the impeller and distal zones can provide for more gradual change in mechanical characteristics to provide for gradual collapse of the cannula, as discussed below.

Figure 5A:
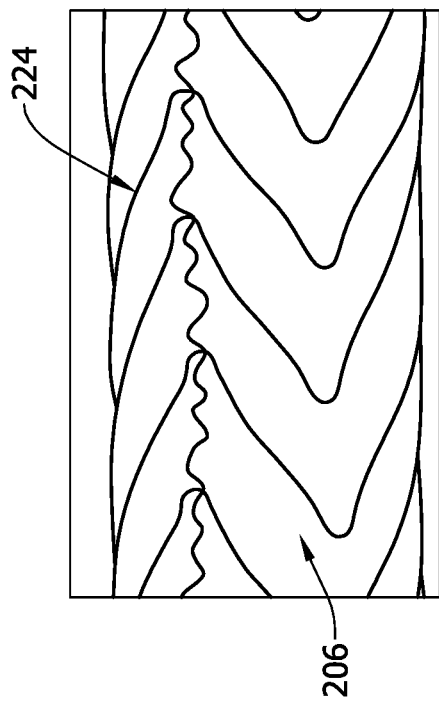
FIG. 5A is a detail view of the distal portion of the formed mesh structure of FIG. 5.

FIG. 5 shows an expanded mesh structure 204 formed of the pattern 200. The mesh structure 204 comprises a plurality of spaced apart helical zones 260. The helical zones 260 are formed by adjacent struts 236 that have less or no movement relative to each other during expansion, where connectors 228 are provided. Adjacent struts that are connected by connectors 228 tend to move or expand less than struts that are not so connected, or do not move or expand at all. FIGS. 5 and 5A shows that the helical zones 260 are in the impeller zone 212 and not in the distal zone. The helical zones 260 provide enhanced concentration of material around the proximal apices 232B of circumferential members 224 in the impeller zone 212. Enhanced concentration of material provides enhanced local stiffness around the proximal apices 232B, which provides greater stiffness and protects the proximal apices 232B and connectors disposed thereon from fracture. As discussed more below in connection with FIG. 12, in some variants proximal apices in a zone (e.g., a distal zone) are omitted but the helical zones are induced to preserve this protective structure around the proximal apices. Such arrangements aid in the re-sheathing of a cannula incorporating this structure.

Enhanced concentration of material (e.g., increased struts per unit area) makes the connection between the apices 232B and adjacent proximal circumferential member 224 more robust. In particular, larger forces are encountered in the impeller zone 212 during collapsing of, sometimes referred to as re-sheathing of, the cannula, e.g., after the catheter pump has been used.

Figure 17:
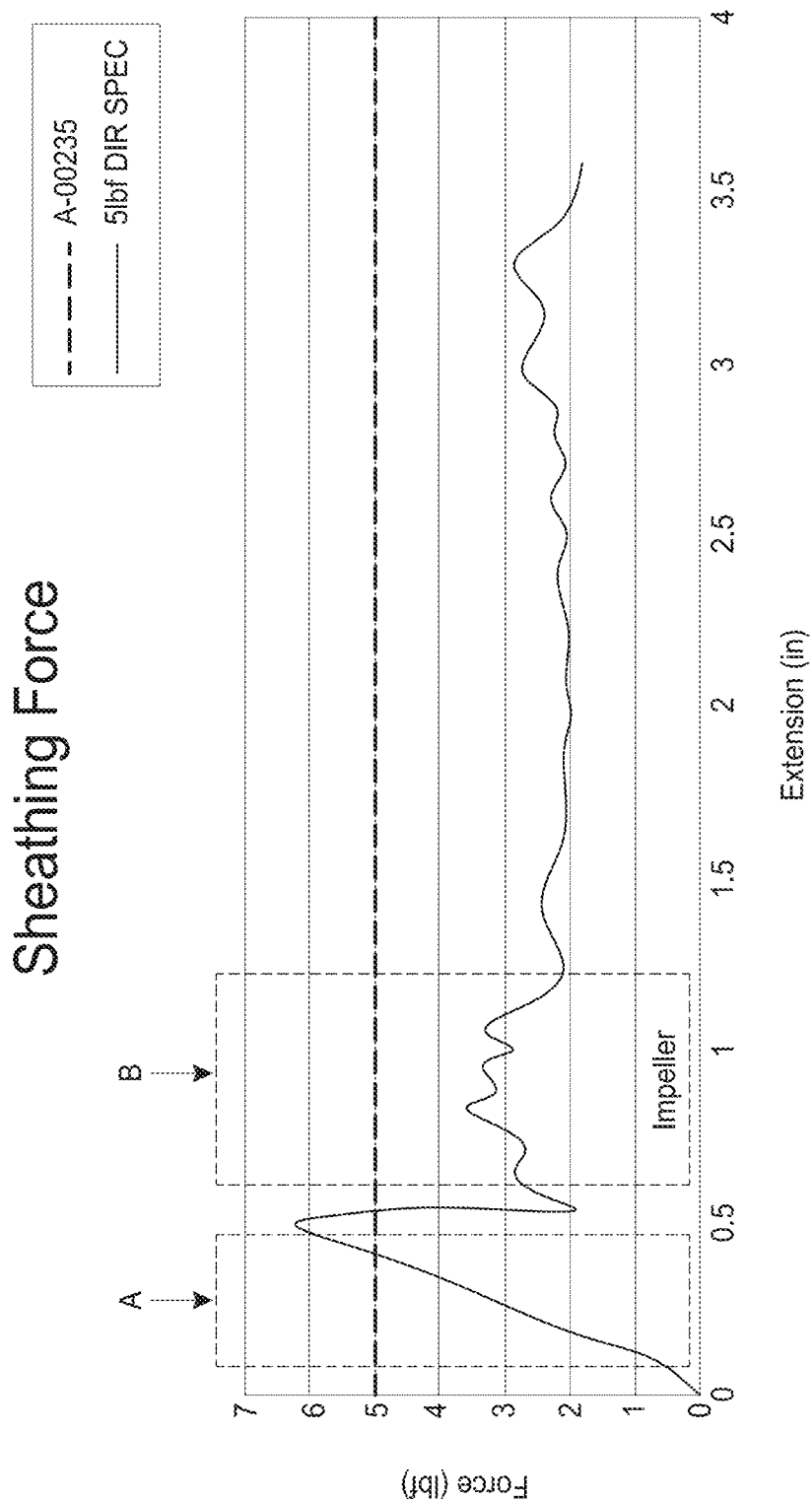
FIG. 17 is a graph of the sheathing force for collapsing a cannula and an impeller for an example wall pattern.

FIG. 17 shows a graph of axial force that may be required to be applied to an outer sheath, such as by the sheath assembly 88, disposed about the catheter body 120 (see FIG. 2) as the sheath assembly is advanced distally along the cannula. This figure shows that in region A the force is relatively high when the distal end of the sheath initially engages the proximal end of the expanded zone of the cannula. The force also increases in a region B to a relatively high level when the distal end of the outer sheath is advanced to a location over the proximal end of the impeller. At each of these locations, the clinicians will note increased resistance to advancement of the sheath to collapse the impeller and/or the cannula and to draw the impeller and/or the cannula into the outer sheath, sometimes referred to herein as re-sheathing. From this graph, an increased risk of failure of one or more connections within the mesh of the cannula being tested has been discovered in these regions of local maxima. Surprisingly, however, various cannulae that have been tested have failed in the lower force region to the right of region B. As a result, there is a surprising benefit to be obtained in enhancing the robustness of the cannula in a region distal of the impeller zone. As discussed herein, the robustness can be enhanced in any one or all of a variety of ways, such as shortening axially oriented connectors between adjacent circumferential members, increasing material per unit area in a region around proximally oriented apices, providing an expanded configuration in which struts of the mesh are positioned close together around a weak point in the mesh structure, and other ways described herein.

FIGS. 4-5A and other embodiments herein illustrate some specific ways of improving the reliability of an expandable cannula, which can help to minimize the risk of breakage within the mesh, e.g., breakage of the connectors 252A. A first technique is making the connectors 252A shorter than the connectors 252. A second technique involves the enhanced concentration of material around the proximal apices 232B, discussed above.

The distal zone 208 is substantially free of the helical zones 260 or other concentration of material in the embodiment of FIG. 4-5A. In the distal zone 208, the struts 236 expand substantially symmetrically about the apices 232A forming a more uniform expanded mesh in the distal zone 208. This arrangement enhances the overall flexibility of the distal zone 208, which can be beneficial. Also, this arrangement makes local zones of the expanded mesh structure 204 substantially uniformly flexible. A mesh structure 204 with a more flexible distal zone 208, and more uniform flexibility, can provide a cannula with a reduced risk of irritating the inner structures of the heart when deployed.

Figure 6:
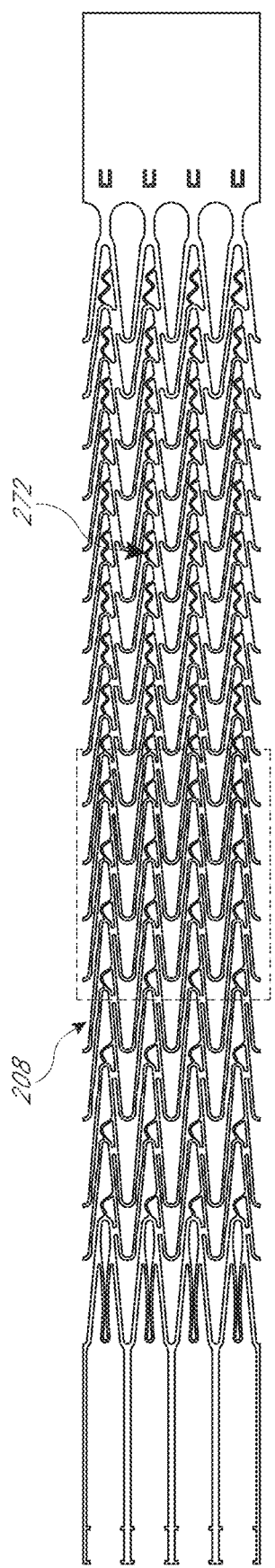
FIG. 6 illustrates another wall pattern of a mesh structure in a flat configuration, where the mesh structure is configured to minimize fracture risk.
Figure 6A:
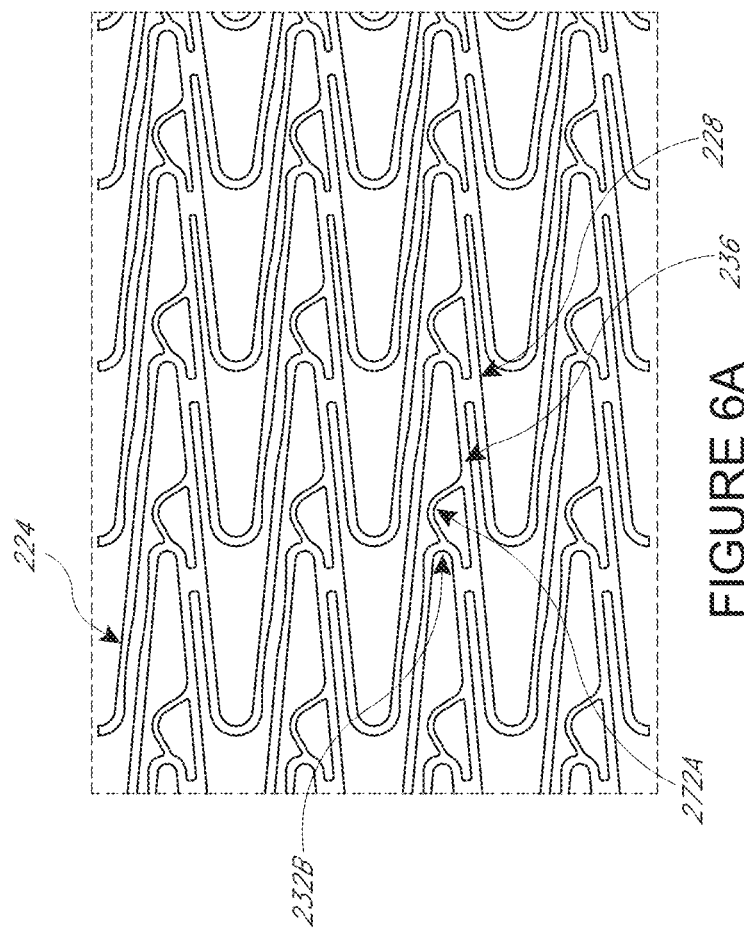
FIG. 6A is a detail view of a distal portion of the wall pattern of FIG. 6.

FIG. 6 shows an embodiment, in which the distal zone 208 is modified to minimize a risk of fracturing connectors in the distal zone. For example, a first plurality of axial connectors 272 is disposed between a proximal side of a proximal apex 232B and a distal side of an adjacent circumferential member 224 in the impeller zone 212. FIG. 6A shows a second plurality of axial connectors 272A is disposed between a proximal side of a proximal apex 232B and a distal side of an adjacent circumferential member 224 in the distal zone 208 of the cannula. In the illustrated embodiment, connectors 272A are provided between proximal apices 232B and a middle portion of the elongate members 236. The axial connectors 272A of the second plurality have first and second ends, and a singe curved section therebetween. In contrast, the axial connectors 272 of the first plurality have first and second ends, and a plurality of curved section therebetween. Stated another way, the axial connectors 272 have multiple undulations and the connectors 272A have a fewer undulation, e.g., a singe curved section.

Also, the distal zone 208 can be made less susceptible to fracture by providing circumferential connectors 228 in some embodiments. In the illustrated embodiment, every other elongate struts 236 of a circumferential member 224 in the distal zone 208 is connected to an adjacent elongate struts 236.

Figure 7:
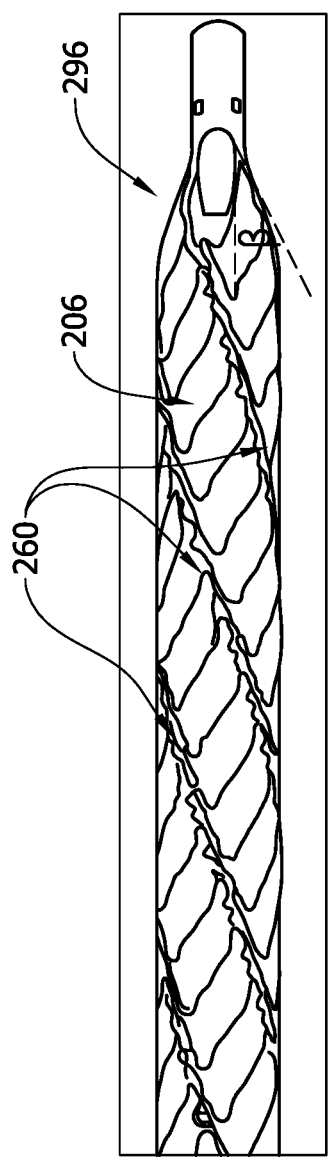
FIG. 7 shows a cannula including a formed mesh structure having the wall pattern similar to that of FIG. 6 covered with a film layer.
Figure 7A:
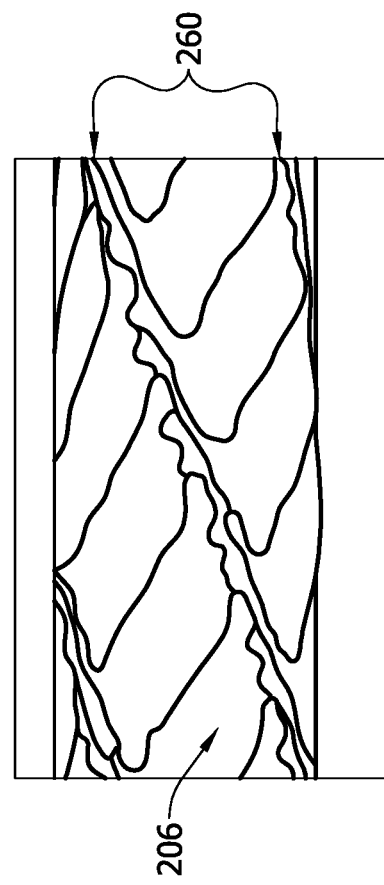
FIG. 7A is a detail view of a distal portion of the cannula of FIG. 7.

FIGS. 7-7A show a cannula 296 incorporating the formed shape of a mesh with some features similar to those of the flat pattern of FIGS. 6 and 6A. In this embodiment the helical zones 260 are provided throughout the cannula 296. In the embodiment of FIGS. 7-7A, apex-to-side connectors each have a plurality of undulations along their length, similar to the connectors 272. However, providing side-to-side connectors 228 throughout the length of the cannula 296 enhances the concentration of material around the apex-to-side connectors. As such, the load applied by the advancement of the sheath over the cannula is spread out over a greater area and a smaller load is concentrated in the apex-to-side connectors. These are examples of techniques for minimizing the chance of fracture of connectors similar to the connectors 272, 272A.

FIGS. 8 and 9 illustrate an embodiment that is similar to that of FIGS. 6 and 7. FIGS. 8 and 9 show a wall pattern 300 and a mesh structure 304 that is configured to provide a good compromise of fracture resistance and flexibility for interaction with heart tissue. The impeller zone 312 has a plurality of circumferential connectors 328 whereas the distal zone 308 is substantially free of circumferential connectors. This provides an impeller zone with spaced apart helical zones, as discussed above, and a distal zone with substantially symmetrical expansion about proximally and/or distally oriented apices thereof. By removing the circumferential connectors in the distal zone, the distal zone is made more flexible. Axial connectors 352 are provided throughout the pattern 300, but the distal zone 308 is provided with axial connectors 352A that are less subject to fracture. For example, the connectors 352A can be limited to fewer undulations than in the connectors 352 in the impeller zone 312, as discussed above.

Figure 10:
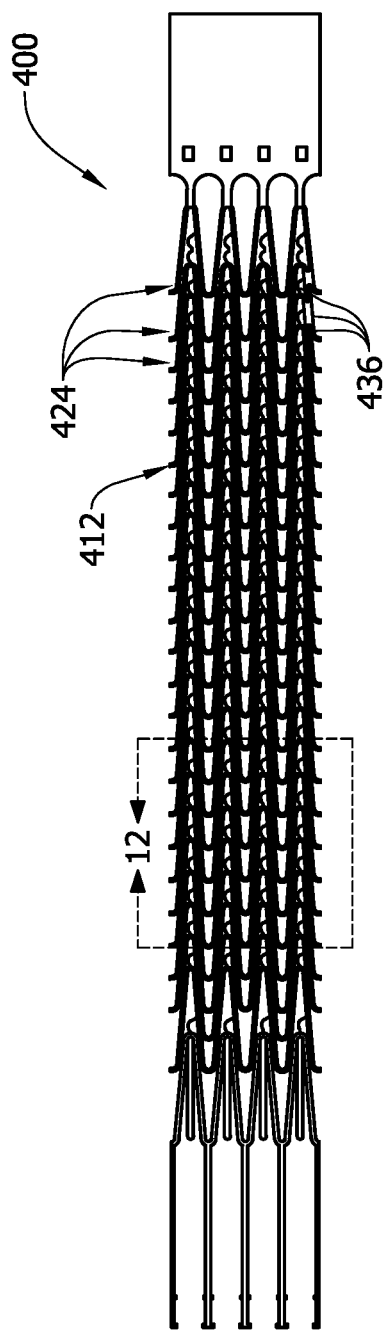
FIG. 10 illustrates another wall pattern of a mesh structure in a flat configuration, where the mesh structure is configured to provide enhanced flexibility in a distal zone, while minimizing fracture risk.
Figure 11:
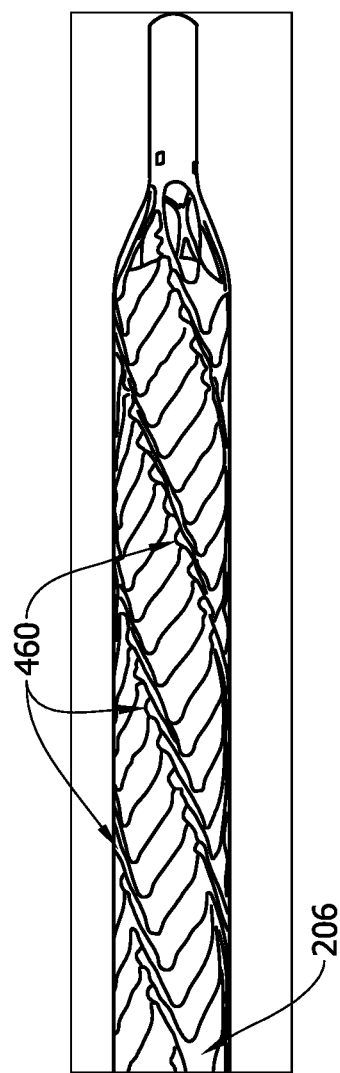
FIG. 11 shows a formed mesh structure for a cannula having the wall pattern of FIG. 10.

FIGS. 10 and 11 illustrate an embodiment that is similar to that of FIGS. 6 and 7. FIG. 10 shows a wall pattern 400 that has a higher concentration of material in the impeller zone 412. Higher concentration of material can be achieved by more tightly packing the apices of the undulating structure of the circumferential members. For example, an angle can be formed between adjacent elongate struts 436 disposed on opposite sides of each of the apices. The angle can be smaller in the embodiment of FIGS. 10 and 11 compared to that of FIGS. 6 and 7. Also, in order to provide more flexibility compared to the pattern of FIGS. 6 and 7, the pattern of FIGS. 10 and 11 omits circumferential connectors in the distal zone 408.

One technique for minimizing fracture risk in the distal zone 408 is to configure the mesh structure 404 to produce helical zones 460 throughout the structure, including in the distal zone 408 where there area no circumferential connectors. This can be achieved by heat setting the expanded shape in a material that would operate in an elastic range in this application. For example, nitinol can be configured to be compressed for delivery and heat set to expand to the shape seen in FIG. 11. This arrangement may provide good flexibility in the distal portion 408 and resistance to fracture of connectors between adjacent circumferential members 424.

Figure 12:
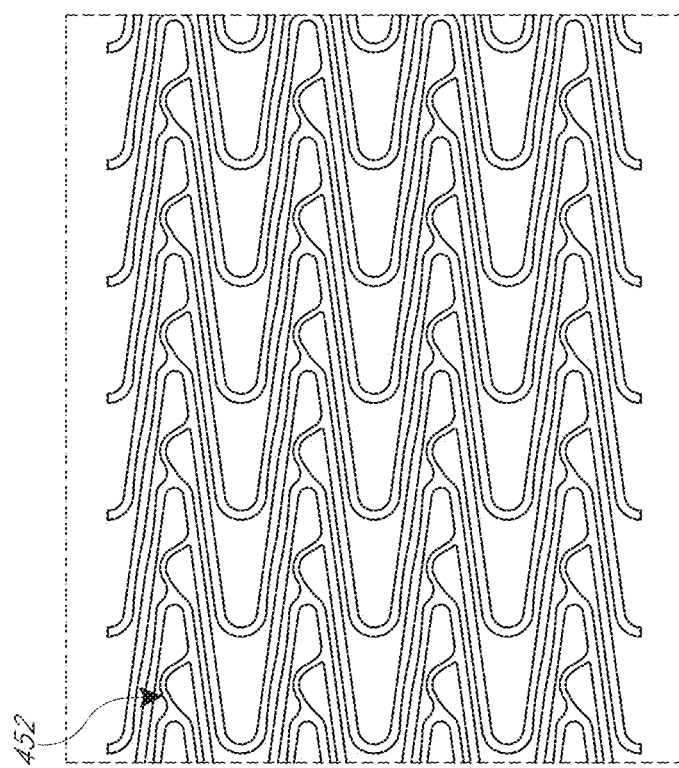
FIG. 12 is a detail view of a distal portion of the wall pattern of FIGS. 8 and 10.
Figures 1, 14A:
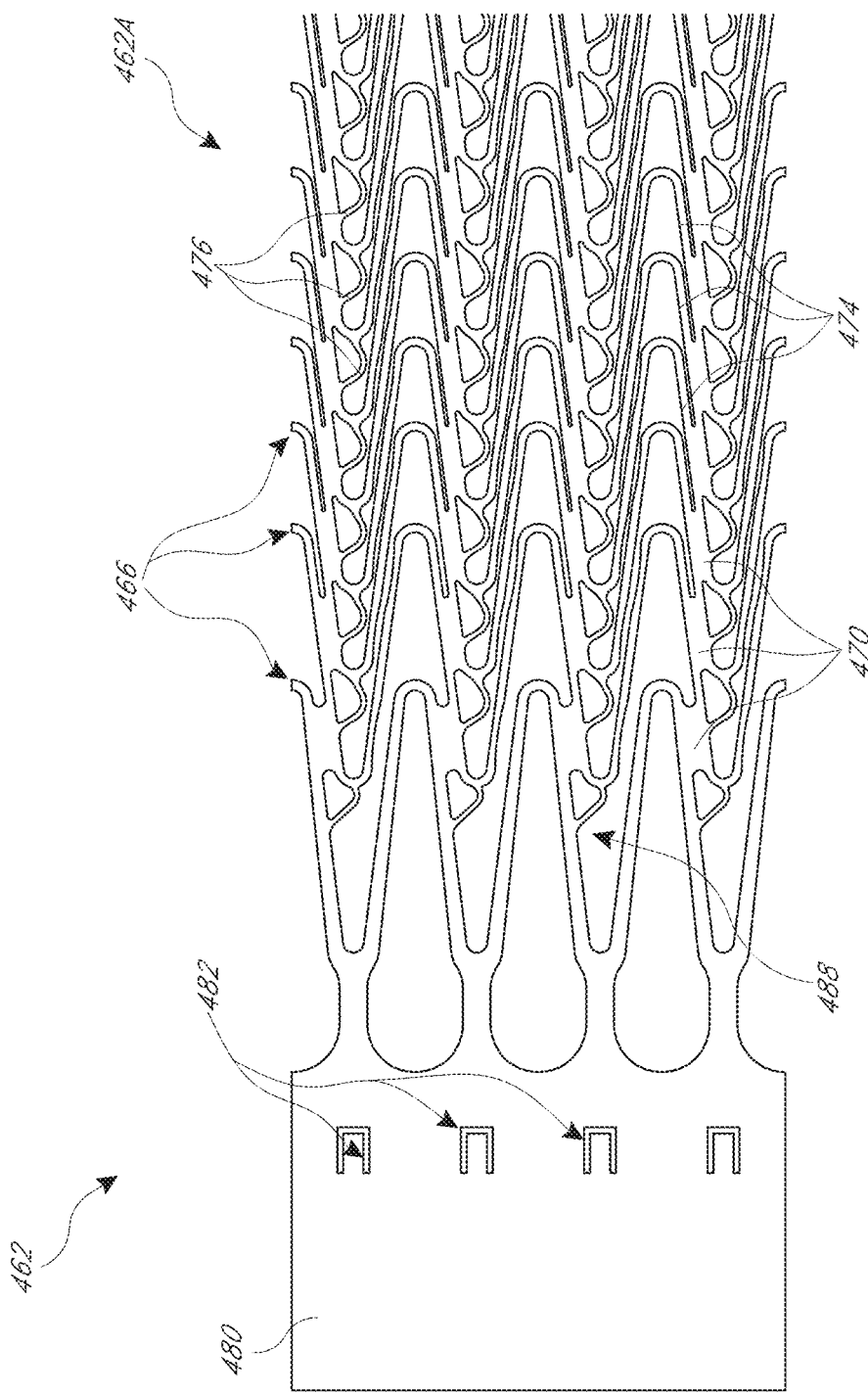
Figures 2, 14A:
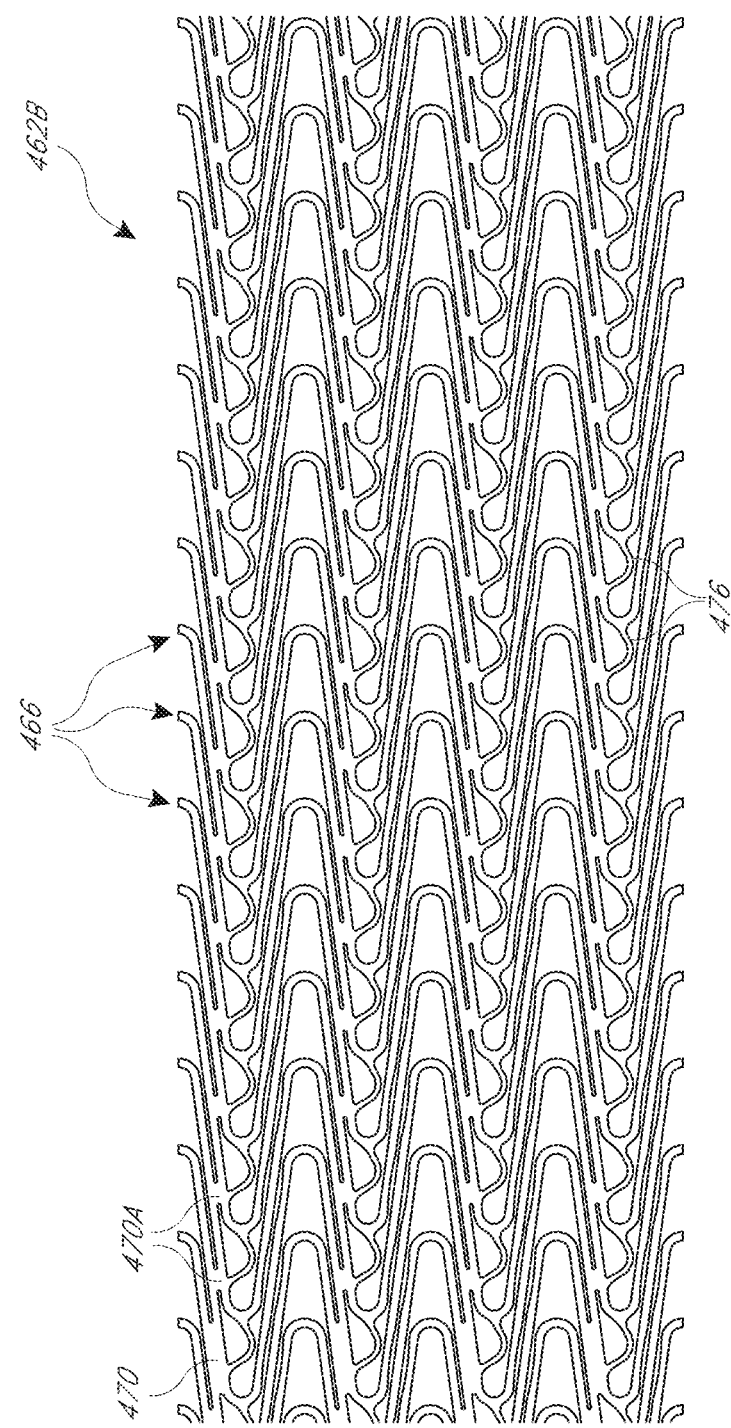
Figures 3, 14A:
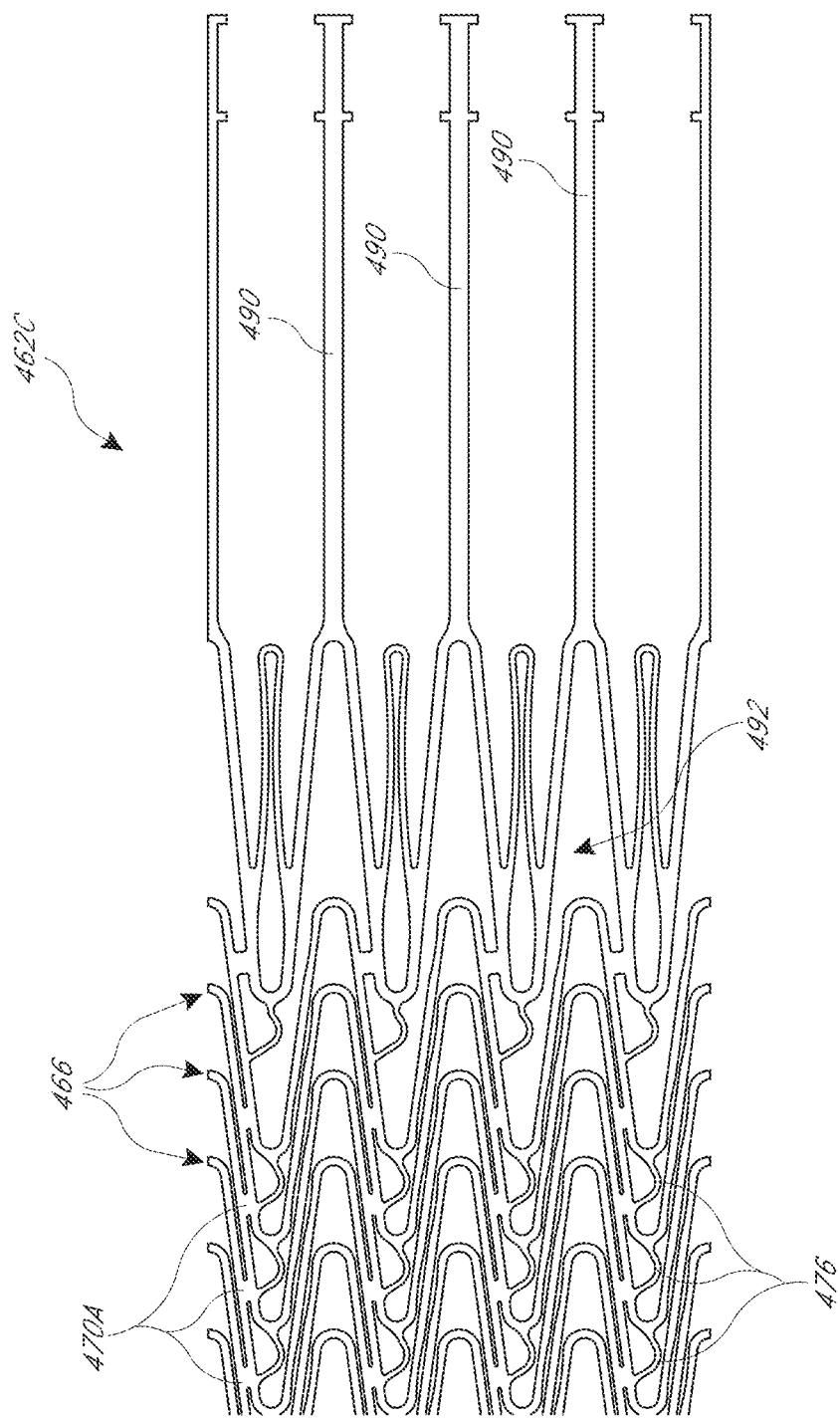

FIGS. 12-14 illustrate an embodiment in which at least a distal zone is configured to be resistant to fracture. FIGS. 12 and 13 show that in one embodiment, short connectors 452 are positioned in the distal zone. The short connectors 452 can be similar to those discussed above, e.g. having only a single curve or inflection between ends thereof. In one configuration, the short connectors 452 can have a length that is no more than about ten times the thickness of the outer sheath used to collapse the cannula. For example, these connectors can be about 0.035 inches long or less. The connectors 452 can be robust in their own right to permit a symmetrical expanded configuration for the distal zone of the wall pattern. Symmetrically expanded apices can provide some advantages, e.g., providing more uniform flexibility with the mesh structure, as discussed above. In some embodiments another technique can be used to spread a load applied by an outer sheath to the cannula incorporating the mesh illustrated in these figures. By spreading the load, the mesh is less subject to fracture.

The pattern arrangements in FIGS. 10-14 also reduce stress and strain on the connectors by subjecting them to more pulling and less twisting during expansion and collapse of the mesh structure. Another advantage of these designs is that they tend to deflect the proximally oriented apices radially inward as the sheath approaches the proximally oriented apices so that a distal face of the sheath does not become lodged beneath the proximally oriented apices. In the heat set distal portion illustrated in FIG. 14, each connector 452 is disposed distal of a portion of an elongate strut 436. The connectors 452 also can be located axially behind the elongate struts 436. In contrast, in the embodiment of FIG. 13, the connector 452 is disposed distal of the nearest proximally oriented apex. The elongate struts 436 in the FIG. 14 embodiment, helps guide the approaching outer sheath over the top of the proximally oriented apices. The elongate struts 436 also locally deflect the cannula in a zone between the connectors 452 and the outer sheath as the sheath approaches individual connectors to minimize any tendency of the connectors 452 deforming around the distal end of the sheath and later breaking.

Another approach to easing re-sheathing involves reducing an amount of open area in the formed cannula wall pattern around relative stiff proximally oriented structures. For example, the axially oriented undulating connectors in FIG. 5A may be more prone to fracture. At least two factors contribute to this. First, these connectors are relatively long. Also, they are surrounded on both sides by large areas not spanned by struts of the mesh pattern. These areas are covered with a polymer material 206 to enclose a cannula. However, upon re-sheathing this polymer material 206 can ride over the outer surface of the outer sheath causing the proximal apices to ride over the outside of the sheath. This can lead to breakage of the axially oriented undulating connectors in FIG. 5A. This is input because the axially oriented connectors are relatively thin in at least one cross-sectional dimension and are formed of somewhat ductile metal. FIG. 13 shows the connectors 452 shortened to minimize this effect. FIG. 14 shows an embodiment in which more struts are placed around at least one side of the short connectors 452 in the helical zones 460. Additionally, circumferential connectors can be provided in the distal zone for this purpose, as discussed herein.

FIG. 14A-1 to 14A-3 show a proximal portion 462A, a central portion 462B, and a distal portion 462C of a wall pattern 462. Each of the portions 462A, B, C has a plurality of circumferential members 466 in a relatively high metal density structure. The circumferential members 466 are close to each other in each of these portions. The members 466 have undulating configurations, e.g., with peaks and valleys. The peaks and valleys of neighboring members 466 can be received within each other, as shown in the figures. The proximal portion 462A is configured to enhance structural integrity of the wall surrounding the impeller. Advantages for this arrangement are discussed above, and include minimizing variation in the gap between the tip of the impeller and the inner wall of the cannula into which the pattern of FIGS. 14A-1 to 14A-3 is incorporated. In the illustrated embodiment, the stiffness of the proximal portion 462A is enhanced by providing a plurality of elongate circumferential connectors 470. The advantages of this sort of connector are discussed above, and include minimizing expansion of elongate struts 474 which are coupled by the connectors 470.

As shown in FIG. 7 an expanded cannula with connectors 470 will have an expanded configuration including spaced apart helical spines that arise from the minimal to no displacement of the struts 474 that are connected by the connectors 470. The spines or other configurations including a connector 470 and a plurality of struts connected thereby advantageously provide areas of enhanced stiffness and/or strength in the wall of a cannula having the pattern 462. Such regions can support an outward load without significant deflection. One outward load that can arise in operation is due to the fluid flowing in the cannula. Although the impeller is configured to primarily drive the blood axially the rotational movement may push blood into the inside wall of the cannula. The spines or other areas of enhanced stiffness can minimize deflection due to this load. Another outward load can be applied by a distal bearing structure such as that described in U.S. patent application Ser. No. 13/802,556, entitled "DISTAL BEARING SUPPORT," now U.S. Pat. No. 9,446,179, incorporated herein by reference in its entirety.

In addition to the connectors 470, 470A, the pattern 462 includes connectors 476 disposed between proximal oriented apices (or valleys, if the pattern is held distal end up) and distal edge of a circumferential member disposed proximally of the apex. The connectors 476 are relatively slender in order to permit the apices to which they are connected to flex upon expansion and collapse of the cannula into which the wall pattern 462 is incorporated. The proximal portion 462A also provides enhanced concentration of material around the connectors 476 to minimize a chance of fracturing these connectors upon expansion and collapse of the cannula.

FIG. 14A-1 illustrates a pattern in the proximal portion 462A providing a high metal density cannula. The pattern has an embedded ring structure, which provides a first ring with a vertex of at least one adjacent ring within the axial length of the first ring. FIG. 14A-1 illustrates embodiments where there are 2 or more adjacent vertices within the axial length of the first ring. There are several benefits of the embedded design for the pump 10. The embedded design provides additional radial strength by increasing the number of load bearing rings per length of cannula. The embedded design minimizes the unsupported film area, which decreases the amount the film can flex as the pressure pulses generated by the impeller pass under it.

Other methods can be used to provide some of these benefits, include making the axial length of the rings shorter and increasing the number of sinusoidal waves within a ring. These features will result in other changes to the cannula pattern. Shorter rings tend to increase the strain the material must undergo in changing from the collapsed to expanded state. Suitable materials, such as nitinol, may be more prone to permanent deformation or fracture with increasing strain. Increasing the number of sinusoidal waves within a ring increases the diameter of the collapsed cannula, if other relevant factors (such as strut width) remains the same, may reduce the stress and strain to which the struts are subjected.

Other cannula patterns can be provided to reduce unsupported film area without increasing the number of embedded rings. For example, an arm feature could be added between two struts of adjacent rings. As the cannula transforms from the collapsed to expanded form, the arm orientation moves from a more axial to more radial orientation (in some cases, forming an "A" shape). More details of these structures are set forth in connection with FIGS. 15-16 below.

In a transition zone between the proximal portion 462A and the central portion 462B, modified connectors 470A are provided that are much shorter in a direction parallel to the longitudinal axis of the struts 474 than are the connectors 470. The shorter connectors 470A make the central portion 462B much more flexible than the proximal portion 462A. Such flexibility can provide less irritation to heart tissue and than higher biocompatibility as discussed elsewhere herein. FIG. 14 shows that the connectors 470A also are provided in the distal portion 462C.

A proximal end of each of the connectors 476 is coupled to a portion of the strut 474 that is also connected to the connector 470 or 470A. This structure provides a concentration of material around the more flexible and elongate connector 476 to minimize the chance of fracture of this structure when the cannula is collapsed by a sheath, as discussed herein. Because the sheathing forces are less in the distal portion of the cannula corresponding to the distal portion 462C, the concentration of material in the distal portion 462C around the connectors 476 can be less than in the proximal portion 462A.

Various additional advantageous features are found on the proximal and distal portions 462A, 472C in various embodiments. For example, when the pattern 462 is formed a sheet-like zone 480 is provided that is advantageous for mechanically integrating the pattern 462 into various catheter bodies in an assembly. A plurality of cantilevered projections 482 is disposed in the sheet-like zone 480 and is disposed about the circumference of the proximal portion 462A when the pattern 462 is formed into a tubular body. The projections 482 can be deflected into mating recesses in the catheter body 84 or another structure of a catheter assembly to provide a resistance to detachment of the pattern 462 (and the cannula into which it is incorporated) from the catheter body or assembly. Such resistance advantageously minimizes inadvertent separation of the cannula from the catheter body 84 during re-sheathing.

Also, the peak-to-peak distance between the proximal-most circumferential member 466 and the circumferential member immediately distal thereof is greater than the average peak-to-peak distance of adjacent circumferential members distal thereof. A consequence of this is that the connector 470 between the proximal-most circumferential member and the adjacent circumferential member is located closer to the peaks of the proximal most circumferential member. This creates an enlarged space 488 that aids in transitioning the diameter of the expanded cannula into which the pattern 462 is incorporated from a larger size disposed about the impeller to the diameter of the sheet-like zone 480 when formed into a tubular body.

The distal portion 462C of the wall pattern includes elongate members 490 that are for mechanically integrating the pattern into a catheter assembly. The elongate members 490 extend from distal apices of the distal portion 462C of the pattern 462. The connectors 470A and 476 disposed between the distal-most circumferential member 466 are shifted closer to the peak of the adjacent circumferential member 466 such that a larger space 492 is provided between the distal-most two circumferential members 466. The shifting of these connectors provides a larger peak-to-peak distance between the distal-most two circumferential members 466 than is provided between other circumferential members of the pattern 462. By increasing this distance, the transition from the enlarged diameter of the expanded cannula into which the pattern is incorporated to the smaller diameter of distally located non-expandable components of a catheter assembly can be facilitated.

Figure 15:
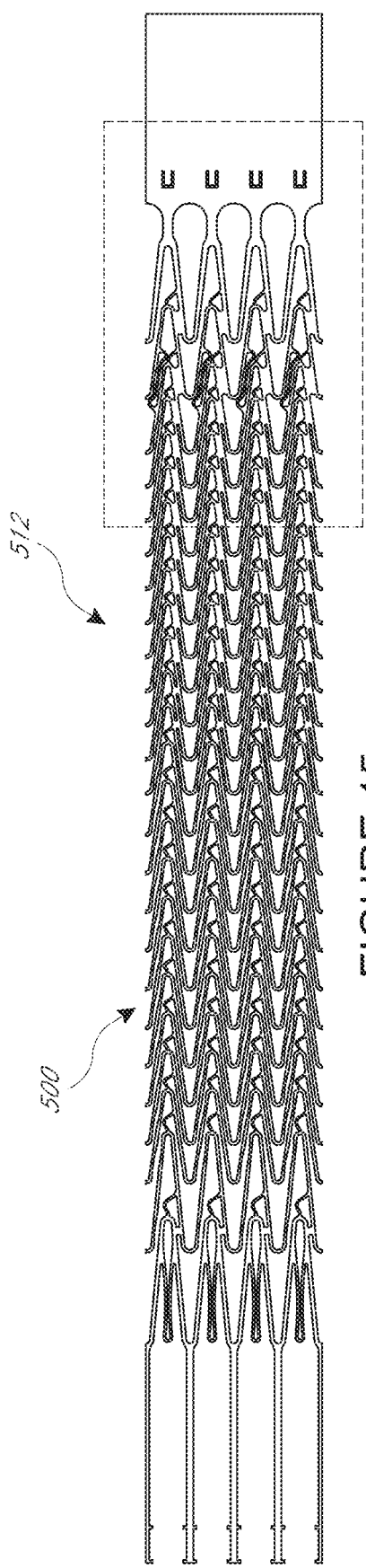
FIG. 15 illustrates another wall pattern of a mesh structure in a flat configuration, where the mesh structure is configured to provide more ports for blood to flow into or out of a cannula formed with this pattern.
Figure 15A:
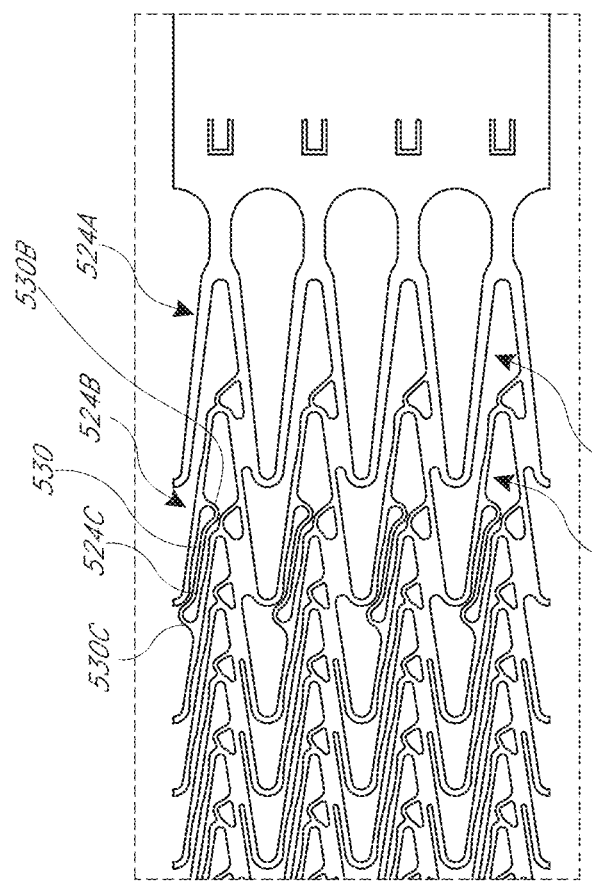
FIG. 15A is a detail view of a proximal portion of the pattern of FIG. 15.

FIGS. 15 and 15A illustrate another embodiment of a wall pattern 500 that can be combined any features of any of the wall patterns herein. These embodiments illustrate a proximal zone of the pattern that forms a transition zone between a non-expandable proximal portion 554 of a cannula and an impeller zone 512. One feature of a cannula formed from the wall pattern 500 is the provision of a larger number of flow passages between inside of the proximal portion of the cannula and outside of the proximal portion thereof. A first outflow area is provided in one embodiment adjacent to the proximal end of the expandable portion of the cannula. In some embodiments, a second outflow area 520 is provided distal of the first outflow area. The first and second outflow areas 518, 520 can take any suitable form. In the illustrated embodiment, the first outflow area is defined between a distal edge or side of a first circumferential member 524A and a proximal edge or side of a second circumferential member 524B.

Figure 16:
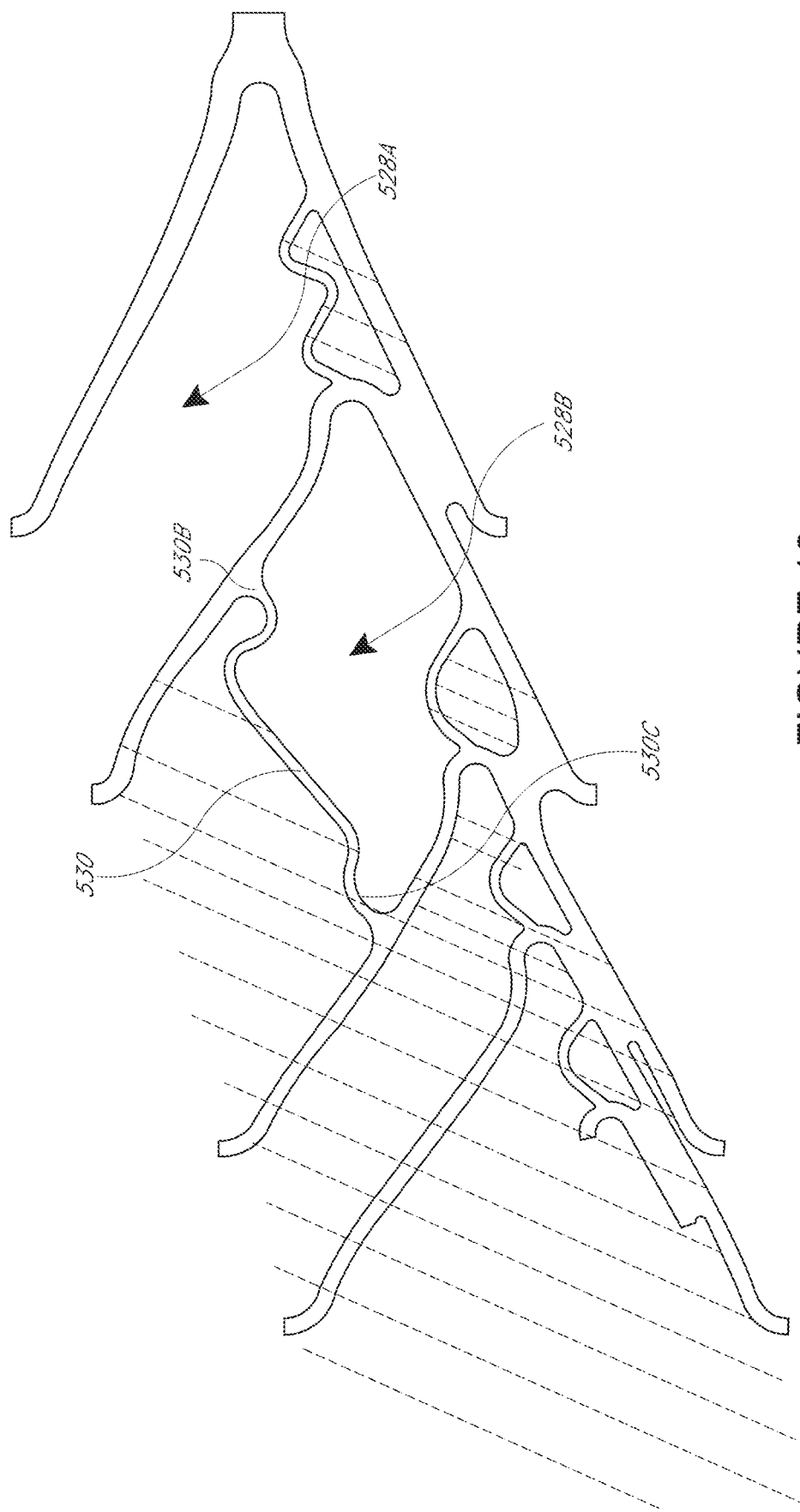
FIG. 16 is an expanded view of the pattern of FIGS. 15-15A.

FIG. 16 shows the expanded configuration of one of a first plurality of openings 528A formed in a mesh. Comparing FIGS. 15A and 16 one can see that the plurality of openings can include four openings 528A formed defined within the members 524A, 524B and connectors extending therebetween. The connectors can take any suitable form, such as those discussed above. In the illustrated embodiment, the second outflow area is defined between a distal side or edge of the second circumferential member 524B and a proximal side or edge of a third circumferential member 524C. More particularly, a plurality of openings 528B in a mesh, e.g. four opening, formed by the pattern 500 are defined within the members 524B, 524C and connectors extending therebetween. The connectors can take any suitable form, such as those discussed above.

FIG. 16 shows a cross-hatched zone distal of the openings 528A, 528B. The cross-hatched zone illustrates the area of the mesh structure that is covered to enclose the space within the mesh structure. Comparing FIG. 16 with FIG. 9, one can appreciate that the openings 528A are inclined with respect to the longitudinal axis of the spaced enclosed therein and the openings 528B are less inclined and in some cases may be disposed on a substantially cylindrical surface about the longitudinal axis of the cannula. In this context, the concept of conforming to a cylindrical surface can be measured when the device is expanded but not implanted or in use. The mesh structure 500 should advantageously provide beneficial flow characteristics compared to an arrangement that only has flow openings 528A. For example, by providing the flow openings 528B (or other variant of a second outflow area 520), the average flow velocity into or out of the cannula can be decreased. By decreasing the average flow velocity, stress on the blood cells can be reduced. Such stresses can be due to shear forces across the boundary into or out of the cannula. Lower stresses on red blood cells can lessen hemolysis or other harm to the blood.

FIGS. 15-16 also illustrate the use of a circumferential connector 530 that is configured to reduce the extent of an unsupported portion of a structure enclosing a lumen within the mesh 500 after the mesh is formed into a cylinder. The connector has a proximal end 530B coupled with a proximal circumferential member 524B and a distal end 530C coupled with a circumferential member 524C that is located distal of the circumferential member 524B. The length of the connector 530 is several times the unexpanded separation distance between the adjacent struts of the circumferential members 524B, 524C. The length of the connector 530 enables the adjacent struts of the circumferential members 524B, 524C to move away from each other to a much greater extent than permitted by the short circumferential connectors 470. In the collapsed state, the connector 530 can be shaped to tightly nestle between the circumferential members 524B, 524C, for example, having a concave portion adapted to receive a portion of a crest of the circumferential members 524B. In some embodiments, the connector 530 enables the adjacent struts of the circumferential members 524B, 524C to move away from each other to the same extent as if these struts were not connected by a circumferential member. See, for example, the struts of the circumferential members that are not connected by circumferential connectors in the expanded cannula shown in FIG. 7A. However, as can be seen in FIG. 16, the presence of the connector 530 greatly reduces the extent of the unsupported area between adjacent struts.

In one embodiment, the connector 530 is connected approximately in the middle of adjacent struts, e.g., half way between adjacent peaks and valleys on each circumferential member. This arrangement roughly reduced by 50 percent the unsupported area between these struts. Long slender struts may be more prone to shearing upon being collapsed into the sheath. Accordingly, it may be desirable to locate the struts 530 in areas of local minima of a sheathing force curve as discussed below in connection with FIG. 17. In other embodiments, the connectors 530 are located away from areas of local maxima of a sheathing force curve as discussed below in connection with FIG. 17.

FIGS. 5, 7, and 17 illustrate further advantageous features of wall patterns. In particular, as noted above, a local maximum in the force-distance curve of FIG. 17 is the region A, which corresponds to a transition zone between the non-expandable part of the mesh and the expandable impeller zone. The test illustrated in FIG. 17 shows that this local maximum exceeds a threshold number that is based on clinician ease-of-use. On technique for reducing the level of this local maximum is to provide a shallower angle of the transition zone. In particular, an angle β can be provided between this inclined surface and a horizontal axis, e.g., an axis parallel to the undeflected longitudinal axis of the cannula. FIG. 7 shows a smaller angle than that of FIG. 5. Preferably the angle β is within a range of from about 30 to about 40 degrees, in some embodiments not more than about 40 degrees. To reduce the force required for re-sheathing, the angle β can be maintained at about 30 degrees or less. The angle β may be maintained above a value that is a function of the trackability of the catheter assembly into which the mesh structure is incorporated. If the angle is too low, the length of the cannula or portions thereof may result in a too stiff cannula to properly track. Another advantage of the shallower angles suggested by FIGS. 7 and 17 is that the impeller zone in a cannula incorporating this pattern is expected to be stiffer. This is one technique for providing better control of a gap between the impeller blade tip and the cannula wall. This tip gap control can advantageously minimize hemolysis and other damage to the blood, as well as any damage to the wall or blades that could be cause by impact therebetween.

The foregoing features of mesh patterns can be combined with other features for improving tip gap control. Such features can be incorporated into a distal bearing, as discussed in U.S. patent application Ser. No. 13/802,556, "DISTAL BEARING SUPPORT," now U.S. Pa. No. 9,446, 179, and/or in impeller or impeller blade construction, as discussed in U.S. patent application Ser. No. 13/802,570, entitled "IMPELLER FOR CATHETER PUMP," now U.S. Pat. No. 8,721,517, both incorporated by reference herein in their entirety.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump assembly, comprising:
   an elongate body having a distal end and a proximal end opposite the distal end;
   an expandable cannula coupled with the distal end of the elongate body, the expandable cannula comprising a mesh structure that includes a plurality of struts defining an impeller zone and a plurality of helical zones extending at least proximate the impeller zone, and a distal zone disposed distally of the impeller zone, wherein the expandable cannula is formed by enclosing a plurality of circumferential members with a polymer, wherein each strut extends one of distally or proximally in an alternating pattern about a circumference of the expandable cannula to define pattern of distally oriented apices and proximally oriented apices;
   an impeller coupled with the distal end of the elongate body and having a stowed configuration and an expanded configuration, the impeller configured to rotate within the impeller zone of the expandable cannula in the expanded configuration to induce fluid flow within the expandable cannula;
   a plurality of circumferential connectors disposed between alternating struts of adjacent circumferential members in at least one of the distal zone and the impeller zone,
   wherein at least one region of the mesh structure further comprises a first plurality of axial connectors each disposed between a proximal side of a proximal apex and a distal side of an adjacent circumferential member in the impeller zone; and
   wherein at least one region of the mesh structure further comprises a second plurality of axial connectors each disposed between a proximal side of a proximal apex and a distal side of an adjacent circumferential member in the distal zone of the cannula.

2. The catheter pump assembly of claim 1, wherein each strut of the plurality of struts is disposed axially adjacent at least one other strut of the plurality of struts.

3. The catheter pump assembly of claim 2, wherein each helical zone of the plurality of helical zones is further defined at least partially between parallel struts of the plurality of struts.

4. The catheter pump assembly of claim 2, wherein each strut extends one of distally or proximally in the alternating pattern to define an undulating pattern of distally oriented apices and proximally oriented apices.

5. The catheter pump assembly of claim 4, wherein the plurality of axial connectors extends between at least one of i) the distally oriented apices or ii) the proximally oriented apices.

6. The catheter pump assembly of claim 1, wherein the plurality of circumferential connectors extends substantially transverse to a longitudinal axis of the expandable cannula between parallel struts of the plurality of struts.

7. The catheter pump assembly of claim 6, wherein a stiffness of the mesh structure is increased at least in the region that includes the plurality of circumferential connectors.

8. The catheter pump assembly of claim 1, wherein each helical zone of the plurality of helical zones extends at least one of i) within the impeller zone, ii) distally of the impeller zone, or iii) proximally of the impeller zone.

9. The catheter pump assembly of claim 1, wherein a material concentration of the mesh structure is greater in the impeller zone than in the distal zone.

10. The catheter pump assembly of claim 1, wherein the mesh structure further defines:
   a first transition zone proximate a distal end of the impeller zone; and
   a second transition zone proximate a proximal end of the impeller zone, and wherein:
   a material concentration of the mesh structure is greater in the impeller zone than in at least one of the first transition zone or the second transition zone.

11. A cannula comprising:
   a self-expandable mesh structure having a proximal end and a distal end, the mesh structure comprising:
      a plurality of struts, each strut of the plurality of struts disposed adjacent at least one other strut and spaced apart axially from the least one other adjacent strut, the plurality of struts extending at least partway between the proximal end of the mesh structure and the distal end of the mesh structure, the plurality of struts defining an impeller zone and a plurality of helical zones extending at least proximate the impeller zone, and a distal zone disposed distally of the impeller zone, wherein each strut extends one of distally or proximally in an alternating pattern to define pattern of distally oriented apices and proximally oriented apices;
      a plurality of circumferential members defining a polymeric enclosure disposed about at least a portion of the mesh structure to define a lumen along a length of the mesh structure between the proximal end and the distal end; and
      a plurality of circumferential connectors disposed between alternating struts of adjacent circumferential members in at least one of the distal zone and the impeller zone,
   wherein at least one region of the mesh structure further comprises a plurality of axial connectors each disposed between a proximal side of a proximal apex and a distal side of an adjacent circumferential member in at least one of the impeller zone and the distal zone.

12. The cannula of claim 11, wherein the impeller zone is configured to expand radially from a first diameter in a stowed configuration to a second diameter in a deployed configuration.

13. The cannula of claim 11, wherein the impeller zone is configured to contain a self-expanding impeller that is configured to induce a flow of blood within the lumen, and whereby the cannula is configured to be included in a catheter pump assembly for pumping blood.

14. The cannula of claim 11, wherein the plurality of helical zones extend axially between the proximal end and the distal end and circumferentially about at least the portion of mesh structure between the proximal end and the distal end.

15. The cannula of claim 11, wherein each axial connector of the plurality of axial connectors is separated from at least one other axial connector by a circumferential gap, the plurality of axial connectors extending at least partway between the proximal end of the mesh structure and the distal end of the mesh structure.

16. The cannula of claim 11, whereby the plurality of helical zones are defined between substantially parallel struts of the plurality of struts.

17. The cannula of claim 16, wherein each strut of the plurality of struts extends one of distally or proximally in an undulating pattern.

18. The cannula of claim 17, the plurality of axial connectors, wherein at least some axial connectors of the plurality of axial connectors extends between at least one of i) the distally oriented apices or ii) the proximally oriented apices.

19. The cannula of claim 11, wherein the plurality of circumferential connectors extends substantially transverse to a longitudinal axis of the cannula between parallel struts of the plurality of struts.

20. The cannula of claim 19, wherein a stiffness of the mesh structure is increased at least in the region that includes the plurality of circumferential connectors.

* * * * *